United States Patent [19]
Klessig et al.

[11] Patent Number: 5,989,846
[45] Date of Patent: Nov. 23, 1999

[54] ASSAYS TO IDENTIFY INDUCERS OF PLANT DEFENSE RESISTANCE

[75] Inventors: Daniel Frederick Klessig, Bridgewater; Zhixiang Chen, Highland Park, both of N.J.

[73] Assignee: Rutgers, The State University of New Jersey, New Brunswick, N.J.

[21] Appl. No.: 08/470,769

[22] Filed: Jun. 6, 1995

Related U.S. Application Data

[60] Division of application No. 08/418,554, Apr. 7, 1995, abandoned, which is a continuation-in-part of application No. 08/259,535, Jun. 14, 1994, abandoned, which is a continuation-in-part of application No. 08/146,317, Nov. 2, 1993, abandoned, which is a continuation-in-part of application No. 08/038,132, Mar. 26, 1993, abandoned, which is a continuation-in-part of application No. 07/923,229, Jul. 31, 1992, abandoned.

[51] Int. Cl.$^6$ ............................... C12Q 1/30; C12Q 1/28
[52] U.S. Cl. ............................... 435/27; 435/28; 435/184
[58] Field of Search .................................. 435/4, 27, 28, 435/69.2, 173.8, 184

[56] References Cited

PUBLICATIONS

*Plant Physiology* Supp. D. (1992), p. 122, "Partial Purification and Characterization of a Soluble Salicylic Acid–Binding Protein From Tobacco Leaves" Chen, Z.

*Environmental Health Perspectives*—"Genetic Modulation of the Cellular Antioxidant Defense Capacity", vol. 88, pp. 77–82, (1990) Amstad, P.

*Plant Cell Physiol.*, "Construction and Expression in Tobacco of β–Glucuronidase (GUS) Reporter Gene Containing an Intron Within the Coding Sequence", 31(6): 805–813 (1990) JSPP, p. 806 Ohta, S.

*Free Rad. Res. Comms.*, vol. 14, Nos. 5–6, pp. 323–334, Association of Antioxidant Systems in the Protection of Human Fibroblasts Against Oxygen Derived Free Radicals—1991 Michiels, C.

*Plant Molecular Biology*, 14: 457–466, (1990) "Inhibition of flower pigmentation by antisense CHS genes: promoter and minimal sequence requirements for the antisense effect" van der Krol, A.

*Proc. Natl. Acad. Sci* USA, vol. 86, pp. 6949–6952, Sep. (1989) "Protection against tobacco mosaic virus in transgenic plants that express tobacco mosaic virus antisense RNA" Powell P.

*Current Biology*, vol. 2, No. 8 Aug. (1992), "A new signalling role for salicylic acid" Hanke P.

*Proc. Natl. Acad. Sci.* USA, vol. 88, pp. 8179–8183, Sep. (1991) Biochemistry, "Identification of a soluble salicyclic acid–binding protein that may function in signal transduction in the plant disease–resistance response" Chen Z.

Landry L., Arabidopsis Mutants Lacking Phenolic Sunscreens Exhibit Enhanced UV–B Injury and Oxidative Damage, Plant Physiol 109:1159–66, 1995.

Chernomorets, M., Diagnosis of Winter Hardiness of Grapevines Using Physiological and Biochemical Indices, Sadovosdstvo, No. 6 pp. 19–24, 1977.

Mehlhorn, H., Ozone Toxicity in Higher Plants and its Modulation by the Environment, Diss Abstracts Int, 50(6) 2320–B, Dec. 1989.

Sanchez–Casas P., A Salicylic Acid Binding Activity and a Salicylic Acid Inibitable Catalase Activity Are Present in a Variety of Plant Species, Plant Physiol 106 pp. 1675–1679, 1994.

Chernomorets, M., Diagnosis of Winter Hardiness of Grapevines Using Physiological and Biochemical Indicies, Sadovosdstvo, No. 6, translation, 1977.

*Primary Examiner*—Ralph Gitomer
*Attorney, Agent, or Firm*—Lerner, David, Littenberg, Krumholz & Mentlik

[57] ABSTRACT

The present invention relates to assays which can be used to identify inducers of plant resistance to pathogens. The assays use catalase and/or ascorbate peroxidase.

4 Claims, 15 Drawing Sheets

| PURIFICATION STEP | TOTAL PROTEIN (mg) | TOTAL ACTIVITY (%) | PURIFICATION FOLD |
| --- | --- | --- | --- |
| CRUDE EXTRACT | 2350 | 100 | 1 |
| DEAE SEPHACEL | 650 | 70 | 2.5 |
| SEPHACRYL S-300 | 70 | 35 | 12 |
| BLUE DEXTRAN AGAROSE | 4 | 26 | 152 |
| SUPEROSE 6 HR 10/30 | 1.5 | 16 | 250 |

ASSAYS TO IDENTIFY INDUCERS OF PLANT DEFENSE RESISTANCE

This is a division, of U.S. Ser. No. 08/418,554, filed on Apr. 7, 1995, which is a Continuation-in-Part application of U.S. Ser. No. 08/259,535, filed on Jun. 14, 1994, which is a Continuation-in-Part application of U.S. Ser. No. 08/146,317, filed on Nov. 2, 1993, which in turn is a Continuation-in-Part application of U.S. Ser. No. 08/038,132, filed on Mar. 26, 1993 which is a Continuation-in-Part application Ser. No 07/923,229, filed on Jul. 31, 1992 all abandoned.

The United States government may have certain rights in the present invention through the National Science Foundation Pursuant to Grant No. DCB-9003711.

TECHNICAL FIELD

The invention relates to the fields of biochemistry and molecular biology and relates to proteins which are capable of binding salicylic acid and like compounds, methods of isolating same and their use. The present invention also relates to the cloning of genes for salicylic acid binding proteins. The present invention also relates to catalase, ascorbate peroxidase, $H_2O_2$ and other active or reactive oxygen species derived from $H_2O_2$ and their role in a plant's disease defense response.

BACKGROUND ART

Perhaps the single best known medication is acetylsalicylic acid—aspirin. Aspirin has long been known to assist in the treatment of pain, swelling and fever. More recently, aspirin has been used to retard blood clotting and lower the risk of heart attacks and strokes.

While the therapeutic value of aspirin has been known for around 100 years, the therapeutic value of closely related compounds dates back far longer. See generally J. R. Cutt and D. F. Klessig, "Salicylic Acid in Plants—A Changing Perspective", *Pharmaceutical Technology*, May 1992, pages 26–33, the text of which is hereby incorporated by reference. For example, Hippocrates in the fourth century B.C. is believed to have prescribed the leaves of willow trees for the relief of pain during childbirth. These leaves contain salicylic acid (also referred to herein as "SA"), a naturally occurring relative of aspirin. Both can be considered part of a broader family of compounds, naturally occurring and synthetic, known as salicylates. While salicylates have long been known to exist in plants, the role that these compounds have played is only now becoming known. For many years, salicylates were classified as secondary metabolites which played no essential role in functioning of the organism. However, more recently, salicylates are gaining recognition as important factors in a number of important plant functions. An expansive, but by no means comprehensive list of plant processes which are affected by salicylates, and in particular, by the addition of salicylic acid thereto is found in Table 1.

TABLE 1

| Process | Effect |
|---|---|
| Flowering | + |
| Thermogenesis | + |
| Alternative pathway | + |
| Glycolysis | + |
| Krebs cycle | + |
| Wound response | − |

TABLE 1-continued

| Process | Effect |
|---|---|
| Disease resistance | + |
| Ethylene biosynthesis | − |
| Potassium ion absorption | − |
| Transpiration | − |
| Stomatal closure | − |
| Leaf abscission | − |
| Seed germination | − |
| Seed germination | + |
| Growth inhibition | + |
| Adventitious root initiation | + |
| Fruit yield | + |
| Somatic embryogenesis | − |
| Photonastic leaflet movement | + |
| Scotonastic leaflet movement | − |
| Gene regulation | + |

+ = induces or enhances
− = reduces or inhibits

It is interesting to note that salicylic acid has been shown to have effects on both the wound response and disease resistance of plants. In this way, plants and animals appear to share some similarities.

Although much remains to be learned about a plant's response to wounds, disease, and the attack by plant pathogens, two specific phenomena have already been observed. First, plants activate a number of a "local" responses in their attempt to restrict the spread of pathogens. This often results in the death of a very limited part of the plant immediately surrounding the site of infection. This is called the hypersensitive or local defense response.

In addition to the local defense response, many plants respond to infection by activating defenses in uninfected parts of the plant. As a result, the entire plant becomes more resistant to secondary infection. This phenomenon, sometimes termed systemic acquired resistance, can persist for some extended period of time and often confers upon the plant a resistance to unrelated types of pathogens.

It is known that adding salicylic acid to certain plants enhances their resistance to disease. It has also been shown that such additions of salicylic acid can induce the expression of the genetic material (genes) within plants to produce certain proteins related to disease resistance. Based on this information and the observation that salicylic acid is not directly toxic to most pathogens under normal conditions, it is believed that salicylic acid participates in a chain of biochemical events which ends in the production of disease combating proteins and possibly other factors or compounds. Salicylic acid may therefore be thought of as a signal molecule in the transduction pathway of plant disease resistance or a link in the chain of events leading to a plant's "immune" response. See Z. Chen and D. F. Klessig, "Identification of Soluble Salicylic Acid-Binding Protein That May Function in Signal Transduction in the Plant-Disease Response", *Proc. Natl. Acad. Sci. USA* 88, 8179–8183, (September 1991), the text of which is hereby incorporated by reference. The fact that when salicylic acid is added to plants, a broad number of plant functions are affected suggests that salicylates or related compounds may be effectors or signal compounds along the transduction pathway of a number of plant functions other than just disease resistance.

The present inventors have identified, purified and characterized a protein which is made by plants. This endogenous protein (endogenous meaning made by the plant) is capable of participating in the binding of salicylic acid in plants. Therefore, it is believed that the endogenous protein may be a link in the transduction pathway of various plant functions such as, for example, disease resistance. Furthermore, the inventors have cloned and sequenced a gene from tobacco which encodes this binding protein.

This discovery is important for a number of reasons. First, the identification of this binding protein, (referred to herein as either "Salicyclic Acid Binding Protein", or "SABP",), is important in gaining a further understanding of the various pathways through which disease resistance, flowering, and other normal plant biological processes function. Furthermore, because salicylates such as aspirin and salicylic acid appear to have advantageous properties in both plants and animals with regard to treatment and/or prevention of disease, it is possible that this discovery will provide information regarding the identification and characterization of parallel mechanisms of, for example, disease resistance in both plants and animals. This could lead to the discovery of new drugs and new forms of treatment for a list of maladies ranging from headaches to high blood pressure. Because of the discovery of this binding protein, the cloning of its gene and the growing understanding of its role in signal transduction, it may be possible to introduce into plants disease resistance mechanisms which might otherwise not be found in that species. It may also be possible to provide enhanced disease resistance, as well as other functions to plants which do use salicylic acid as a signal. The cause of world hunger could also be advanced by such discoveries because disease resistant crops could be generated with reduced incident of crop failure.

The present inventors have discovered that the binding protein that they have isolated and purified exhibits a quantitative and qualitative correlation between binding activities and the physiological activities of salicylic acid compounds. In other words, the more biologically active a salicylate is in a plant, the more tightly it will be bound by the native salicylic acid binding protein of the present invention and vice versa. Therefore, assays or tests can be developed and used as a first step in determining whether certain salicylates, either of natural or synthetic origin, might be biologically active and, therefore, agriculturally or pharmaceutically important, The inventors have discovered that the identified salicylic acid binding protein has catalase activity which is inhibited by binding. Inhibition of catalase's $H_2O_2$-scavenging activity would result in an elevated level of $H_2O_2$ and other reactive oxygen species ("ROS", also called active oxygen species—"AOS"). As used herein the term "catalase" refers to the family of enzymes known as catalases. The previously documented involvement of reactive oxygen species in host defense against microorganisms (Orlandi et al., *Physiol. and Mol. Plant Pathol.* 40: 173 (1992); Schwacke et al., *Planta* 187: 136 (1992); Apostol et al., *Plant Physiol.* 90: 109 (1989); Legendre et al., *Plant Physiol.* 102: 233 (1993); Baker et al., *Plant Physiol.* 102: 1341 (1993)) and the discovery that the salicylic acid binding protein is a catalase whose activity is inhibited by SA. binding suggest that the role of salicylic acid in defense may be through its modulation of the abundance of reactive oxygen species via the influencing of plant catalase activity.

This hypothesis is further supported by additional discoveries. First, the inventors have found that 2,6-dichloroisonicotinic acid (INA), which is a potent synthetic inducer of enhanced disease resistance and of proteins related to disease resistance (Uknes et al., Plant Cell 4: 645 (1992); Uknes et al., Mol Plant-Microbe Interact. 6: 692 (1993)), also inhibits catalase activity. Second, they discovered that both salicylic acid and INA also inhibit the activity of ascorbate peroxidase. As used herein "ascorbate peroxidase" refers to the family of enzymes known as ascorbate peroxidases. Since catalase and ascorbate peroxidase are the two principal enzymes in plants for destruction of $H_2O_2$ (Bowler et al., Annu. Rev. Plant Physiol. Plant Mol. Biol. 43: 83 (1992); Jahnke et al., Plant Cell Environ. 14: 98 (1991)), their inhibition by salicylic acid, INA, or functionally similar compounds would result in elevated levels of $H_2O_2$ and other reactive oxygen species. The fact that both a natural (salicylic acid) and synthetic (INA) inducers of disease resistance inhibit both key enzymes involved in the removal of $H_2O_2$ illustrates that modulation of the level of reactive oxygen species is an important step in the development of disease resistance.

SUMMARY OF THE INVENTION

In accordance with the present invention and in one aspect thereof, there is provided a salicylic acid binding protein having an apparent average native molecular weight of about 180 kDa, an apparent $K_d$ of 14±5 $\mu$M for salicylic acid and being capable of binding alicylic acid compounds in direct correlation with a salicylic acid compound's physiologic activity, said protein being in purified form.

There is also provided, in accordance with this aspect of the present invention, a protein species having an apparent $K_d$ of 14±5 $\mu$M for salicylic acid and being capable of participating in the binding of salicylic acid compounds in direct correlation with a salicylic acid compound's physiologic activity, said protein species resulting from a process including the steps of providing a plant tissue; homogenizing and buffering the tissue to form a homogenate; filtering and clarifying the homogenate and collecting a first supernatant; chromatographically fractionating the first supernatant in a first anion exchange column to yield a first eluent; and chromatographically treating the first eluent in a second gel filtration column to yield a second eluent.

The term "salicylic acid compound(s)" as used herein is meant to encompass salicylic acid and benzoic acid analogues thereof. The term includes, but is not limited to, such compounds as 2-hydroxybenzoic acid (salicylic acid); (acetylsalicylic acid) (aspirin); 2,6-dihydroxybenzoic acid;, 3-hydroxybenzoic acid; 4-hydroxybenzoic acid; 2,3-dihydroxybenzoic acid; 2,4-dihydroxybenzoic acid and 2,5-dihydroxybenzoic acid. See also Table 3.

$K_d$ of 14±5 $\mu$M as used herein is the dissociation constant for the salicylic acid binding protein. $K_d$ is defined herein as the concentration of salicylic acid needed to occupy 50% of the binding sites on the salicylic acid binding protein when the binding process reaches its equilibrium. Thus, a smaller value of $K_d$ indicates a stronger interaction between salicylic acid and salicylic acid binding protein and vice versa. $K_d$ is determined by measuring the amounts of salicylic acid bound to salicylic acid binding-protein at various concentrations of salicylic acid and then plotting the ratio of bound to free, salicylic acid concentrations versus bound salicylic acid concentrations to give a linear plot with a slope of $-1/K_d$.

The phrase "apparent average native molecular weight" indicates the average molecular weight as determined by gel filtration. Although these molecular weight determinations may not be as precise as those obtained by SDS-PAGE analyses, they do represent a measurement of the molecular weight of the native binding protein as opposed to, for example, a denatured species. See Example 3. Further, the term "salicylic acid binding protein" as used herein includes not only the specific protein identified in the immediately preceding section, i.e. the native or naturally occurring species, but also derivations and analogues thereof which are capable of binding salicylic acid compounds as defined herein.

As alluded to previously, salicylic acid appears to be an effector or signal molecule which is produced in plants. Salicylic acid when present in a plant or, in fact, when added to a plant, can broadly affect a number of plant processes. These processes include inducing the expression of genes which produce anti-pathogenic compounds such as glucanases, chitinases, and permatins. The influence of salicylic acid is, therefore, significant with regard to disease resistance in plants. As shown in Table 1, other salicylic acid influenced functions include flowering, thermogenesis, and fruit yield.

The salicylic acid binding protein characterized by the inventors has also been shown to have catalase activity. Catalases are present in all organisms which grow aerobically and convert the reactive oxygen species $H_2O_2$ to $H_2O$ and $O_2$. During the rapid and intense oxidative burst associated with pathogen or elicitor treatment in plants ((Orlandi et al., *Physiol.* and *Mol. Plant Pathol.* 40: 173 (1992); Schwacke et al., *Planta* 187: 136 (1992); Apostol et al., *Plant Physiol.* 90: 109 (1989); Legendre et al., *Plant Physiol.* 102: 233 (1993); Baker et al., *Plant Physiol.* 102: 1341 (1993))) elevated levels of reactive oxygen species (ROS) are thought to be generated by plasma membrane-localized NAD(P)H oxidases. The inventors have shown that plants appear to utilize ROS for subsequent development of Systemic Acquired Resistance (SAR), and that the mechanism of ROS generation is unique. Rather than producing $H_2O_2$ via oxidases, they block breakdown by catalases of $H_2O_2$, which is constitutively synthesized as a byproduct of several metabolic pathways (e.g. photorespiration and β-oxidation of fatty acids). This difference may reflect the plant's energy consciousness since the increase of $H_2O_2$ associated with SAR occurs throughout the plant where $H_2O_2$ is a byproduct while the rapid oxidative burst that requires energy takes place only in a small number of cells around the site of infection. The inventors have also discovered that salicylic acid will inhibit the $H_2O_2$ scavenging activity of ascorbate peroxidase.

The discovery of a salicylic acid binding protein has a number of important implications with regard to a wide variety of plant functions. Salicylic acid binding protein (SABP), in its native form, may be introduced into a plant by genetic engineering. For example, using standard molecular biological techniques, the gene(s) encoding the salicylic binding protein can be genetically engineered into plants to modify plant phenotype, response to disease, and other salicylic acid mediated responses. The gene can either be expressed in sense orientation to increase the abundance of the protein or in antisense orientation to reduce the level of endogenous salicylic acid binding protein. Thus, the characteristics of salicylic acid binding can be modified in such a way as to influence salicylic acid-influenced plant functions.

The sense or antisense SABP gene can be expressed in different tissues by using tissue or cell-specific promoters to drive expression and to modify salicylic acid-influenced responses in a tissue or cell-specific manner without affecting tissues in which the selected promoter is not expressed.

The foregoing discussion was based on plants which have a salicylic acid-influenced transduction pathway amongst their signaling mechanisms. But the applicability of the present invention is not limited thereto. It is possible to genetically engineer a salicylic acid transduction pathway including the mechanisms for producing salicylic acid binding protein and other downstream elements of the salicylic acid transduction pathway into a plant. This would provide to the plant specific characteristics not otherwise naturally occurring therein. For example, a foreign gene whose product helps protect a plant against disease and whose promoter (naturally or through genetic engineering), contains an element which makes it activatable by salicylic acid, could be introduced into a plant by standard molecular biological techniques. Simply by applying salicylic acid to the plant at an appropriate time (e.g. at the first sign of pathogen infestation), the gene would be induced to produce its protective compound. In this way, a complete salicylic acid or salicylic acid like transduction pathway can be introduced into a plant.

The discovery of the salicylic acid binding protein of the present invention also allows for the development of biochemical assays. These assays can be developed for screening novel biologically or physiologically active analogues of salicylic acid which would fall under the general heading of salicylic acid compounds as defined herein. For example, an assay could be developed based on the ability of a salicylic acid compound to bind to naturally occurring salicylic acid binding protein or to compete with salicylic acid for binding to the protein. Thus, these assays will allow for testing and comparing the activities of various salicylic acid compounds. In addition, known catalases could be used in screens using a similar procedure aimed at identifying compounds which may inhibit catalase activity. Ascorbate peroxidase could be used in a similar screen aimed at identifying compounds which may inhibit ascorbate peroxidase activity. Assays of the kind described above will be useful in the identification of new chemical compounds which might modulate the host plant's resistance to, disease.

The present inventors have also discovered that the compound 2,6-dichloroisonicotinic acid (INA), like salicylic acid, has the ability to bind SABP/catalase and ascorbate peroxidase. Like salicylic acid, INA is known to induce resistance to a variety of pathogens (Metraux et al., In Advanced in Molecular Genetics of Plant-Microbe Interactions 1: 432, 1991, Kluwer Academic Publishers, Dordrecht; Ward et al., Plant Cell 3: 1085, 1991 Uknes et al., Plant Cell 4: 645, 1992) and to induce expression of a common set of genes in the systemic acquired resistance response (Ward et al., Plant Cell 3: 1085, 1991). The inventors have demonstrated that INA, like salicylic acid, functions in inducing acquired resistance by binding and inhibiting the catalase activity of SABP/catalase and by inhibiting ascorbate peroxidase. Thus, the screening assays referred to above can be directed towards the identification of any compounds which modify catalase activity or modify ascorbate peroxidase activity or modify both activities and these compounds could be analogues of salicyclic acid, analogues of INA or structurally different compounds with no relation to either salicylic acid or INA, but which exert a cellular effect by modifying catalase and/or peroxidase activities. A particularly interesting use of such assays is in the identification of compounds which inhibit catalase or ascorbate peroxidase to a similar or greater extent than do salicylic acid or INA and which may have great utility as inducers of acquired resistance for plant pathogen resistance.

In addition to the method for identifying compounds which bind the SABP more strongly than salicylic acid and which may therefore modify the function of the SABP and thus modify salicylic acid-based responses, it is also possible to modify the SABP itself for modified binding of specific compounds including endogenous salicylic acid. For example, modification of the coding sequence of the SABP can be undertaken, and the resultant protein expressed in E. coli using techniques well known in the art. The modified SABPs thus generated can be assayed in vitro for differential affinity of binding of salicylic acid and other compounds; this would be determined by comparison of the compounds to unmodified SABP. Modified SABPs which are bound more tightly by salicylic acid and other compounds will be identifiable, as well as modified SABPs to which these same compounds exhibit reduced affinity.

Of course, a salicylic acid-like pathway can be developed including analogues of salicylic acid and a modified complementary binding protein. By so doing, it is possible to render a specific plant's function, such as disease resistance, more efficient. For example, plants may have internal mechanisms which negatively affect or inactivate salicylic acid. This may be done as part of the normal cellular mechanism to control the amount of salicylic acid available at any given time. The present invention may offer a solution. It has been discovered that a salicylic acid-glucoside exists in plants. J. Malamy, J. Hennig, and D. F. Klessig, "Temperature-dependent induction of salicylic acid and its conjugates during its resistance response to tobacco mosaic virus infection". Plant Cell 4 (1992) 359–366. This discovery, coupled with observations that several plant hormones are inactivated by conjugation with glucose, suggests that an internal mechanism which negatively affects or inactivates salicylic acid exists in plants. Either the introduction of an analogous pathway into the plant, or the application to the plant of a salicylic acid analogue which can bind to salicylic acid binding protein, but which will not be affected by the plant's inactivation mechanism could increase the efficiency for induction of a salicylic acid-like response in the plant.

It may also be possible to genetically engineer into a plant a system which parallels the naturally occurring salicylic acid transduction pathway but which is based on discrete and non-competitively binding analogues. In that way, the normal salicylic acid based cellular functions of a plant will continue undisturbed. However, increases in newly introduced functions can be induced. The plant which contains thus complementary salicylic acid binding protein analogue and other downstream mechanisms necessary for salicylic acid-induced expression can be induced to express by the application to the plant of the non-competitive salicylic acid compound analogue. The salicylic acid analogue can then bind to the modified salicylic acid binding protein analogue. Plant functions will therefore be influenced by two discrete transduction systems.

It will be clear from the above description of the invention that it is possible to modify certain cellular functions. For example, the insertion of a dominant-negative mutation into the plant genome encoding a SABP which has been modified such that it no longer binds salicylic acid will result in a SABP which fails to transduce the salicylic acid signal. As the inventors have shown that the SABP functions in a multimeric complex, then a complex containing both functional and non-functional SABPs will likely not transduce the salicylic acid signal. An alternative approach which would provide the same result would be the overexpression of a wild-type gene encoding a form of catalase which is not inhibited by salicylic acid, but which is capable of assembly with the endogenous catalase-sensitive form(s). In contrast, overexpression of a catalase gene in which the active site has been modified blocking catalase activity, but not the ability of the polypeptides to assemble with other subunits may cause the opposite result, i.e.", elevated levels of the ROS signal, even in the absence of SA.

Expression of the unmodified SABP in antisense orientation behind a strong promoter will also result in a failure to transduce the salicylic acid signal, that is salicylic acid binding protein-based cellular functions can be modified by blocking the production of salicylic acid binding protein. In this technique, the genetically engineered salicylic acid binding protein gene is expressed (transcribed) in the opposite direction relative to the endogenous or normal gene. This results in the synthesis of antisense RNA which is complementary to the sense or normally occurring mRNA which would normally encode salicylic acid binding protein. These two complementary RNAs hybridize or base pair together to form an RNA duplex which is poorly translated into protein or which is destroyed by specific enzymes within the plant. The end result is that very little salicylic acid binding protein is produced from the endogenous salicylic acid binding protein gene. A similar approach using expression of the ascorbate peroxidase gene(s) in an antisense orientation behind a strong promoter will also result in a failure to transduce the salicylic acid signal.

A third approach to modify salicylic acid binding protein-based cellular functions utilizes production of large amounts of a salicylic acid binding protein analogue that binds salicylic acid, perhaps even more tightly than the naturally occurring protein. The binding protein analogue would have no physiological activity. However, the salicylic acid binding protein analogue could bind all or most of the salicylic acid produced by or added to a plant thereby interrupting the salicylic acid signal. In this way, little or no salicylic acid is available to facilitate salicylic acid induced responses, whether or not these responses are in fact mediated by salicylic acid binding protein.

Table 1 shows that salicylic acid causes a variety of plant responses. In some cases (such as disease resistance) salicylic acid induces the response, whereas in other cases it inhibits the response. The cloning of the SABP gene means that it is now possible to enhance and alter these responses by modifying the salicylic acid induced pathway. Using techniques which reduce the abundance of SABP (e.g. antisense), techniques which modify the binding of salicylic acid to SABP (using dominant negative mutations or salicylic acid insensitive forms of catalase), and techniques which increase the abundance of SABP, it will be possible to modify these responses both positively and negatively. In one embodiment, a modified SABP could be expressed in a plant. Such modified SABPs are capable of assembling with endogenous SABPs to form inactive enzymes.

The present invention also has implications with regard to animals including humans. While the medicinal effects of aspirin (and salicylic acid) are well established in animals, there is no evidence that salicylic acid affects gene expression in animals or that animals contain a protein analogous to the salicylic acid binding protein described here. This presents the possibility of developing a new inducible gene expression system in animals based on salicylic acid and its salicylic acid binding protein. The gene encoding the salicylic acid binding protein, under control of an appropriate promoter, could be introduced into animals. Production of the salicylic acid binding protein could make the transformed animal responsive to exogenously applied salicylic acid. For example, a gene could be introduced into the animal that contained a promoter which had cis acting elements which allowed it to respond to its appropriate salicylic acid signal. Thus in the presence of salicylic acid and its salicylic acid binding protein, it should respond. Since salicylic acid is nontoxic in most animals and powerful cis acting salicylic acid responsive elements have been identified, this could be an excellent system for inducing high level expression of foreign genes. There is precedence for transfer of inducible gene expression systems between very divergent organisms. For example, the GAL4 system found in yeast has been shown to work in plants and animals. See (J. Ma et al., "Yeast activators stimulate plant gene expression", Nature, 334 (1988) 631–633; and H. Kakidani and M. Ptashne, "GAL4 activate gene expressions in mammalism cells." Cell 52 (1988) 161–167.)

In accordance with another aspect of the present invention, there is provided a binding species selected from the group consisting of a protein having a molecular weight of 48 kDa when measured by SDS-PAGE, and a protein having a molecular weight of 150 kDa when measured by SDS-PAGE, at least one of which having a $K_d$ of 14±5 $\mu$M for salicylic acid and being capable of participating in the binding of salicylic acid compounds in direct correlation with a salicylic acid compound's physiologic activity, said protein being in purified form.

Similarly, in accordance with another aspect of the present invention, there is provided the protein species resulting from the process just described which also includes the steps of chromatographically fractionating said second eluent on a third gel filtration column to yield a third eluent; and chromatographically fractionating said third eluent on a fourth immobilized reactive dye column to yield a fourth eluent; and collecting said fourth eluent.

The native salicylic acid binding protein of the present invention is, as previously described, a protein having an apparent average native molecular weight of approximately 180 kDa. It is this binding protein which actively binds salicylic acid in normal plant systems. However, the native binding protein need not be a single protein. In fact, the binding protein of the present invention may be composed of smaller proteins which are not "capable of binding salicylic acid" as individual units. However, at least one of the smaller proteins is capable of participating in binding salicylic acid. For example, one of the protein species may be capable of actually binding to salicylic acid. Other component proteins are capable of participating in binding to the extent that they provide some structural support or a particular orientation to the actual binding species.

It is also possible that the smaller proteins exist as a homomeric or heteromeric complex, one or all of which is both capable of binding to salicylic acid and/or participating in the binding as previously described.

Another aspect of the present invention is the provision of methods for obtaining, in a more purified form, salicylic acid binding protein. One such method includes the steps of providing a plant tissue; homogenizing and buffering said tissue to form a homogenate; filtering and clarifying said homogenate and collecting a first supernatant; chromatographically fractionating said first supernatant in a first anion exchange column to yield a first eluent; and chromatographically fractionating said first eluent on a second gel filtration column to yield a second eluent.

The process may also include the steps of chromatographically fractionating said second eluent on a third gel filtration column to yield a third eluent; chromatographically fractionating said third eluent on a fourth cation exchange column to yield a fourth eluent; chromatographically fractionating said fourth eluent on a fifth gel filtration column to yield a fifth eluent; and collecting said fifth eluent.

Alternatively, the process may include the steps of chromatographically fractionating said third eluent on a fourth immobilized reactive dye column to yield a fourth eluent. The fourth eluent may be further fractionated as desirable.

Another aspect off the present invention is the cloning and sequencing of a gene from tobacco which encodes the binding protein.

BRIEF DESCRIPTION OF THE DRAWINGS

Preferred embodiments of the present invention will be described in greater detail with reference to the accompanying drawings where.

BEST MODE OF CARRYING OUT THE INVENTION

The salicylic acid binding protein of the present invention can be isolated from plant tissue by the use of a unique combination of separation steps. The steps involved include providing a plant tissue, homogenizing and buffering the plant tissue to form a homogenate, filtering the homogenate and collecting the first supernatant following centrifugation. Thereafter, the first supernatant is chromatographically fractionated on a first anion exchange column. The first eluent from the first fractionation step is again chromatographically fractionated on a second gel filtration column.

Plant tissue as used herein refers to any plant tissue from any member of the plant kingdom which contains salicylic acid binding protein. As shown in Table 2, a wide variety of plants have shown salicylic acid binding activity indicating the presence of salicylic acid binding protein. These include, without limitation:

TABLE 2

| Plant | Activity |
| --- | --- |
| Tobacco | + |
| Cucumber | + |
| Tomato | + |
| Maize | + |
| Soybean | + |
| Arabidopsis | + |

Other plants which are expected to exhibit such activity include: casaba, guava, papaya, oil palm, rubber, canola, sunflower, rye, beans, ginger, lotus, bamboo, potato, rice, peanut, barley, malt, wheat, alfalfa, oats, eggplant, squash, onion, broccoli, sugar cane, sugar beets, beets, apples, oranges, grapefruit, pear, plum, peach, pineapple, grape, rose, carnation, daisy, tulip, douglas fir, cedar, white pine, scotch pine, spruce, peas, cotton, flax and coffee.

By the term plant tissue, it is also understood that any part of a plant might be used, including the stem, flower, leaf, trunk, root, seed or any subparts thereof. Homogenization of plant tissues can be accomplished with a polytron homogenizer or tissue blender in a homogenization buffer, whose components are specified below.

Figure 3A:
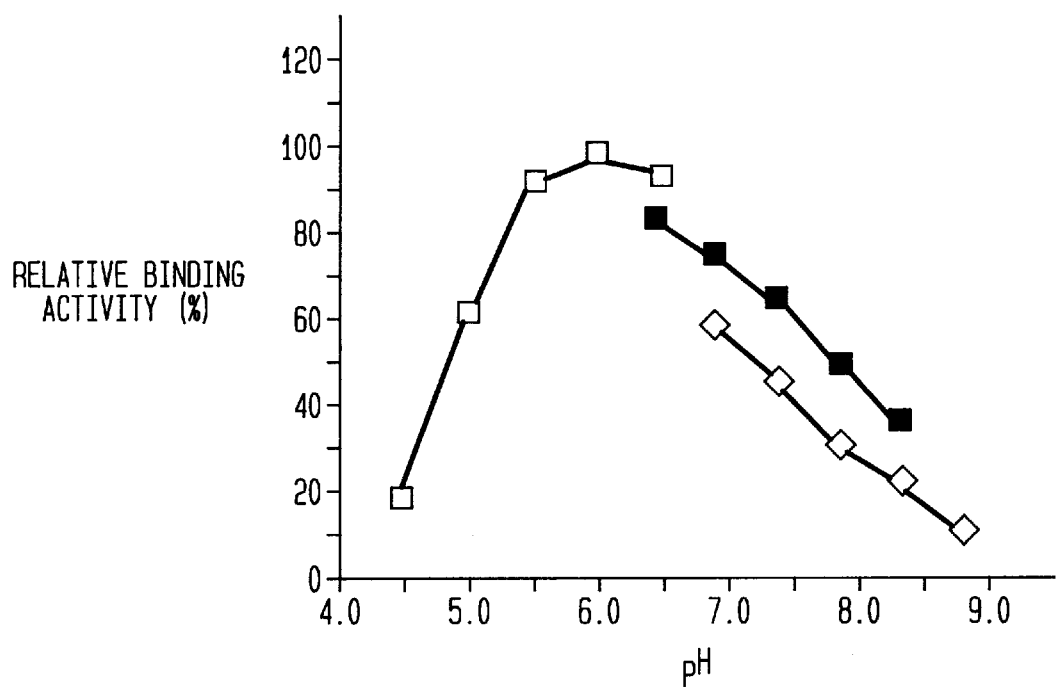
FIG. 3A is a graph of relative binding activity (%) of native salicylic acid binding protein as a function of pH where (□) represents citrate, (■) represents phosphate/Na+, and (◊) represents Tris/Na+.

Buffering can be accomplished using any known buffer. Of course, it is preferred to use buffers which are biochemically compatible. Salicylic acid binding proteins have been found to bind in a pH-dependent manner with an optimum pH ranging from between about 5.5 to about 6.5. See FIG. 3A. The pH of the homogenized plant tissue should be maintained in a range of between about 5 to about 9 and preferably in a range of between about 5.5 to about 7. Suitable buffers include tris buffers, phosphate buffers, citrate buffers and combinations thereof. The buffer may also contain magnesium chloride, glycerol, phenylmethylsulfonyl fluoride and polyvinylpolypyrrolidone.

The buffered homogenate is then filtered to remove cellular debris such that a substantially liquid supernatant is formed. Any method of separation can be used in this regard. However, filtering through four layers of cheesecloth followed by centrifugation for 40 minutes at 40,000 g has been shown to be effective.

Thereafter, the supernatant, termed the first supernatant, is collected and fractionated on an anion exchange column, termed the first anion exchange column. One type of anion exchange column useful in accordance with the present invention is a diethylamino ethyl (DEAE)-cellulose column which has been equilibrated with the same buffer used to form the homogenate minus polyvinylpolypyrrolidone. The supernatant is loaded onto the column and the column is washed extensively with the buffer. Salicylic acid binding protein is eluted from the column by the use of the same buffer containing a linear gradient of a salt such as potassium chloride. Fractions containing the highest level of salicylic acid binding activity (hereafter referred to as peak fractions) are then pooled for subsequent steps. Other types of anion exchange columns useful in accordance with the present invention include aminoethyl (AE) and quaternary aminoethyl (QAE) columns, and the like. Other salts such as sodium chloride, sodium acetate, potassium acetate, ammonium chloride, and ammonium acetate could be used for elution.

Figure 4:
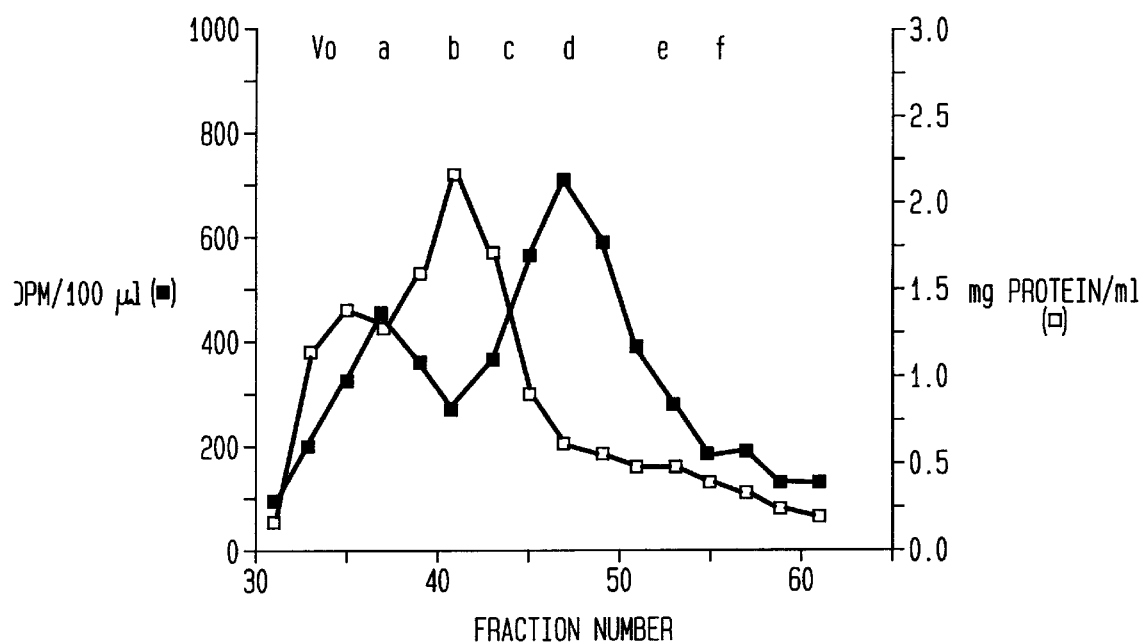
FIG. 4 is a graph of the salicylic acid binding activity profile resulting from gel filtration chromatography used to determine the apparent average native molecular weight of the binding protein. (□) represents total protein eluted and (■) represents binding activity eluted.

The first eluent, which results from chromatographically fractionating the first supernatant on the first anion exchange column is then further chromatographically fractionated on a second gel filtration column to yield a second eluent. The term "second", as used in conjunction with the gel filtration column is meant to indicate that this is the second column employed, not that a first gel filtration column was used in a prior step. In a preferred embodiment, the fractions with highest binding activity (peak fraction) which had been pooled as the first eluent are concentrated via $N_2$-aided filtration concentrator and are loaded onto a sephacryl 5–300 gel filtration column, which is equilibrated with the buffer previously used. The samples are eluted in the same buffer and the fractions are then assayed for both protein content and salicylic acid binding activity. Other gel filtration columns useful for the same purposes include Sephadex G-200, Sepharose 6B/Sepharose CL-6B and Superose 6HR 10/30. In addition to further fractionating the sample, the second gel filtration column also provides an opportunity to obtain the apparent average native molecular weight of the salicylic acid binding protein. The pooled peak fractions from the first anion exchange column were loaded onto the second gel filtration column and eluted at a flow rate of 40 milliliters per hour at 4° C. Fractions were assayed for salicylic acid binding activity using, for example, 15 μM of [$^{14}$C] salicylic acid. The elution volumes of six molecular mass standards, as well as the bed volume and the void volume of the column were determined under the same conditions and a calibration curve was obtained. For a more detailed discussion of molecular mass estimation, see Z. Chen and D. F. Klessig, "Identification of a soluble salicyclic acid-binding protein that may function in signal transduction in the plant disease-resistance response", *Proc. Natl. Acad. Sci. USA,* 88, 80, (September 1991). See also Example 3. The resulting species was found to have an apparent average native molecular weight of approximately 180 kDa. FIG. 4 illustrates the results, both in terms of total protein eluted from the gel filtration column and binding activity, i.e. salicylic acid binding protein. As FIG. 4 aptly illustrates, it is possible to obtain good separation and, therefore, purification of the salicylic acid binding protein by the methods described above. It was also shown that there are two peaks of binding activity: fractions 33–49 and having an apparent average native molecular weight of 650 kDa and a second peak eluting in fractions 45–49, and having an apparent average native molecular weight of 180 kDa. It is believed that the 650 kDa species is an aggregate of the 180 kDa salicylic acid binding protein of the present invention. In prior reported work, specifically Z. Chen and D. F. Klessig cited immediately above, the 650 kDa species was isolated to the exclusion of the 180 kDa salicylic acid binding protein. The discrepancy in the results illustrates the importance of the various separation protocols used. In the Chen and Klessig articles, ammonium sulfate precipitation was used instead of an anion exchange column separation as used herein.

The binding protein also exhibited a $K_d$ of $14\pm5 K_d$ $\mu$M. $K_d$ of $14\pm5$ $\mu$M values were determined by Scatchard analysis with [$^{14}$C] salicylic acid concentrations ranging from 2 to 70 $\mu$M. Scatchard analysis of $K_d$ is done by measuring the amounts of salicylic acid bound to the salicylic acid binding proteins at various concentrations of salicylic acid and then plotting the ratio of bound to free salicylic acid versus the concentration of bound salicylic acid to yield a linear Scatchard plot with a slope of minus $1/K_d$.

The 180 kDa native binding protein isolated was tested for binding affinity and specificity. A competitive assay was established using salicylic acid binding protein fractionated from plants as previously described. As shown in Table 3, [$^{14}$C] salicylic acid (20 $\mu$M) was assayed in the presence of 40 $\mu$M (2×) or 200 $\mu$M (10×) of an unlabeled competitor.

TABLE 3

| Competitor | Biological activity | Inhibition (%) 2× | 10× |
|---|---|---|---|
| Salicylic Acid Compounds | | | |
| 2-Hydroxybenzoic acid (SA) | ++ | 50 | 91 |
| 2,6-Dihydroxybenzoic acid | ++ | 51 | 91 |
| Acetylsalicylic acid* | ++ | 25 | 57 |
| Benzoic acid | + | 14 | 25 |
| 2,3-Dihydroxybenzoic acid** | ± | 1 | 10 |
| 3-Hydroxybenzoic acid | − | −2 | 0 |
| 4-Hydroxybenzoic acid | − | 1 | −2 |
| 2,4-Dihydroxybenzoic acid | − | −1 | −2 |
| 2,5-Dihydroxybenzoic acid | − | 1 | −1 |
| 2,3,4-Trihydroxybenzoic acid | − | 1 | 2 |
| 2,4,6-Trihydroxybenzoic acid | − | −1 | 3 |
| 3,4,6-Trihydroxybenzoic acid | − | 1 | −1 |
| 3-Aminosalicylic acid | − | 1 | 5 |
| 4-Aminosalicylic acid | − | 0 | −1 |
| 5-Aminosalicylic acid | − | 1 | −2 |
| Thiosalicylic acid | − | −5 | 1 |
| 2-Chlorobenzoic acid | − | 0 | 2 |
| 2-Ethoxybenzoic acid | − | −3 | 2 |
| Catechol | − | 0 | 1 |

*Activity of acetylsalicylic acid is probably due to conversion to salicylic acid, the latter of which is both biologically active and capable of binding.
**Low level of physiologic activity found in some assays and correspondingly low binding activity.
"++" indicates a high level of biological activity.
"+" indicates a lower level of biological activity.
"±" indicates low, but detectable biological activity in some assays.
"−" indicates no biological activity.

Biological activity was based upon values reported in Abad et al., "The effect of benzoic acid derivatives on Nicotiana Tobacum growth in relation to PR-b1 production", Antiviral Res. 9, (1988), 315–327; L. C. Van Ooon, "The induction of pathogenesis-related proteins by pathogens and specific chemicals", Neth. J. Plant. Pathol., 89, (1983), 265–273; R. F. White, "Acetylsalicylic acid (Aspirin) induces resistance to tobacco mosaic virus in tobacco", Virology, 99, (1979) 410–412; R. F. White et al., "The chemical induction of PR-(b) proteins and resistance to TMV infection in tobacco", Antivir. Res., 6, (1986), 177–185; H. M. Doherty et al., "The wound response of tomato plants can be inhibited by aspirin and related hydroxybenzoic acids", Physiol. Mol. Plant Pathol., 35 (1988) 377–384.

As shown in Table 3, only biologically active salicylic acid compounds (salicylic acid, 2,6-dihydroxybenzoic acid, and aspirin and benzoic acid) were able to effectively compete with the [$^{14}$C] salicylic acid for binding salicylic acid binding protein in accordance with the present invention. Salicylic acid which has not been radioactively labeled showed an incidence of inhibition of approximately 50% when the binding assay involved a mixture containing a 1:2 ratio of labeled to unlabeled salicylic acid. When the amount of unlabeled salicylic acid used was ten times that of the radioactive species, as expected, the percent inhibition became approximately 90%. Similar behavior was observed from 2,6-dihydroxybenzoic acid which is about as biologically active as salicylic acid.

2,3-dihydroxybenzoic acid has a very low level of binding. It has a correspondingly low level of biological activity. Aspirin is also capable of binding and has biological activity. Its activity and binding are greater than 2,3-dihydroxybenzoic acid but lower than salicylic acid. In some assays aspirin has lower biological activity than salicylic acid or 2,6-dihydroxybenzoic acid (J. Raskin et al. "Regulation of heat production in the inflorescences of an Arum lily by endogenous salicylic acid", Proc. Natl. Acad. Sci. USA 86 (1989) 2214–2218) and accordingly is less capable of competing with salicylic acid for binding. As shown in Table 4 aspirin is not actually bound by the salicylic acid binding protein. Rather it is readily hydrolyzed (cleaved) either spontaneously or enzymatically to produce salicylic acid. The level of biological activity and binding is therefore attributable to the salicylic acid released by hydrolysis. Benzoic acid as discussed herein is both somewhat biologically active and capable of binding.

TABLE 4

Binding of [$^{14}$C] salicylic acid, [Carboxyl-$^{14}$C].acetylsalicylic acid and [Acetyl-$^{14}$C] acetylsalicylic acid by Partial Purified Salicylic Acid Binding Protein
Binding was assayed with 3 mg/ml of the partially purified salicylic acid binding protein and the listed concentration of each ligand with the same specific radioactivity (9.9 Ci/mol). Values were obtained from three independent binding assays and are reported with the sample (n = 3) standard deviations.

| | [$^{14}$C] radioactivity bound (dpm/100 $\mu$l) | |
|---|---|---|
| Assay Condition | with protein | without protein |
| 50 $\mu$M [acetyl-$^{14}$C] | 96 ± 10 | 104 ± 9 |
| 50 $\mu$M[carboxyl-$^{14}$C] acetylsalicylic acid | 397 ± 25 | 112 ± 10 |
| 50 $\mu$M [$^{14}$C] salicylic acid | 989 ± 78 | 89 ± 7 |

Figure 6A:
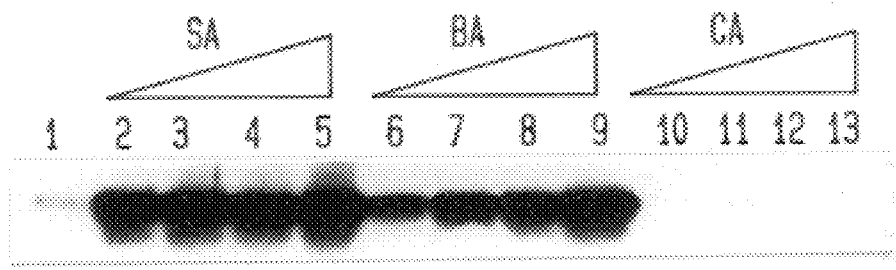
FIG. 6A is a representation of the ability of salicylic acid (SA), benzoic acid (BA) and O-coumaric acid (CA) to induce PR1 expression.
Figure 6B:
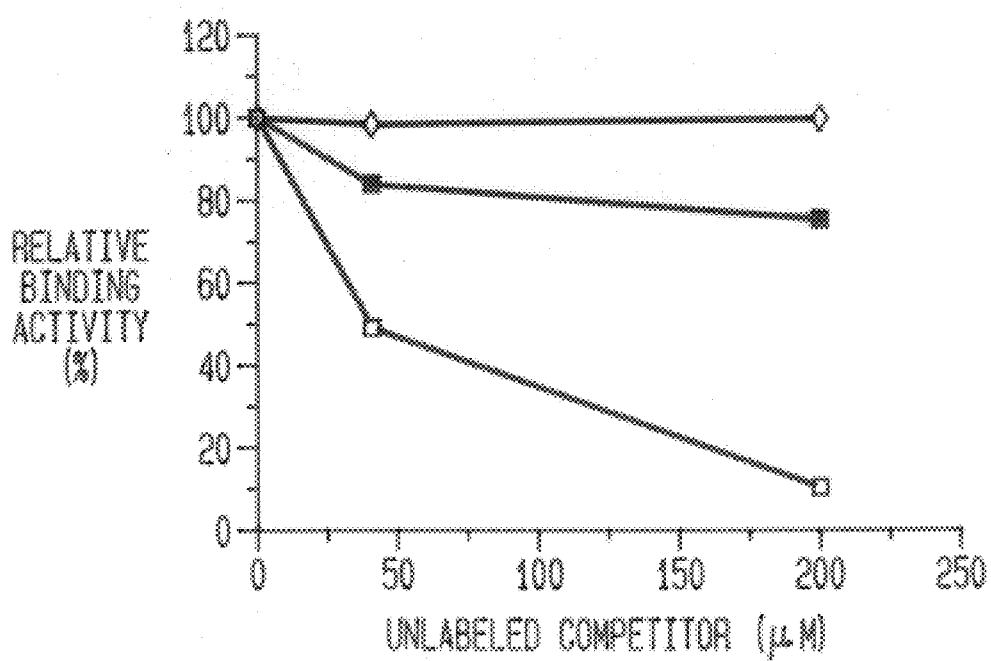
FIG. 6B is a graph of the relative ability of salicylic acid (□), benzoic acid (■), or O-coumaric acid (◊) to compete with a labeled [$^{14}$C] salicylic acid for binding with native salicylic acid binding protein.

As further support for the proposition that salicylic acid binding activity is capable of binding both quantitatively and qualitatively in terms of the biological activity of the bound substance, binding assays were conducted using two proposed salicylic acid precursors, benzoic acid and O-coumaric acid. Benzoic acid has been shown to induce plant disease resistance only in concentrations higher than salicylic acid (R. F. White, "Acetylsalicylic acid (Aspirin) induces resistance to tobacco mosaic virus in tobacco virology" 99 (1979) 410–412) and as shown in FIG. 6A, benzoic acid was able to induce the expression of PR1 genes in tabacco. But higher concentrations (approximately ten-fold) of benzoic acid than salicylic acid are required to induce similar levels of PR1 gene expression. This alone suggests that benzoic acid has a reduced biological activity compared to salicylic acid. O-coumaric acid did not induce PR1 gene expression at concentrations of up to 10 mM, indicating that O-coumaric acid is biologically inactive.

In a competitive binding assay, as shown in FIG. 4B, benzoic acid inhibited [$^{14}$C] salicylic acid binding about 20% as well as unlabeled salicylic acid. This is consistent with the fact that higher concentrations of benzoic acid than salicylic acid were required to induce similar levels of PR1 expression. O-coumaric acid was unable to compete for binding to salicylic acid binding protein. This is consistent with the fact that O-coumaric acid has no known biological activity. Thus, there is a quantitative, as well as a qualitative, correlation between biological or physiological activity and binding activity.

Figure 3B:
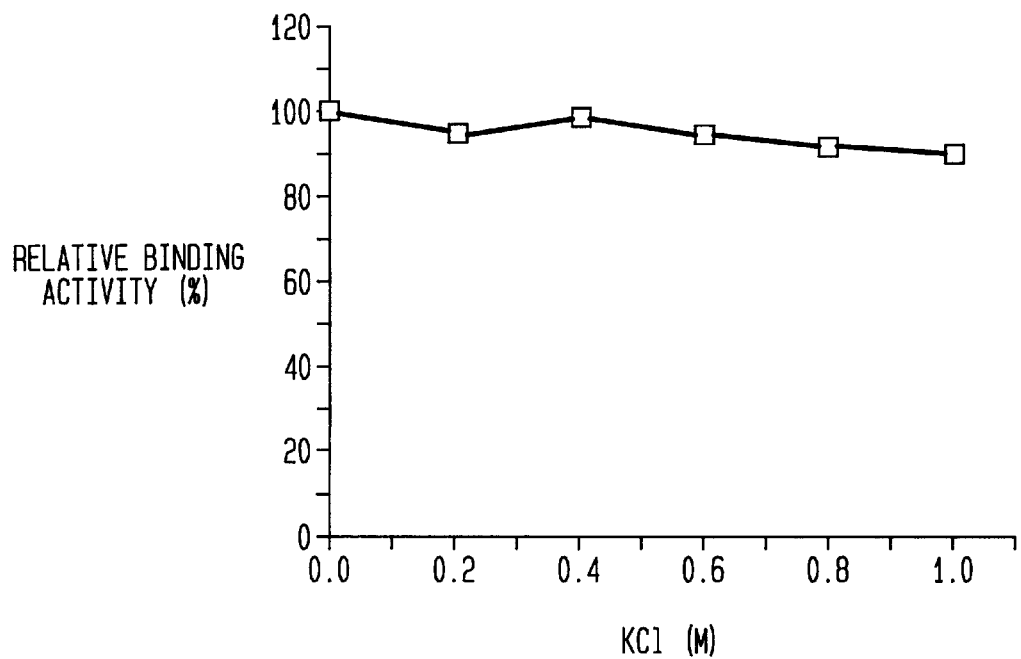
FIG. 3B is a graph of relative binding activity (%) of native salicylic acid binding protein as a function of ionic strength.

The salicylic acid binding activity of the native salicylic acid binding protein in accordance with the present invention appears to be independent of salt concentration. As shown in FIG. 3B, increasing KCl concentration to 1.0M did not significantly reduce the binding activity thereof.

Figure 5:
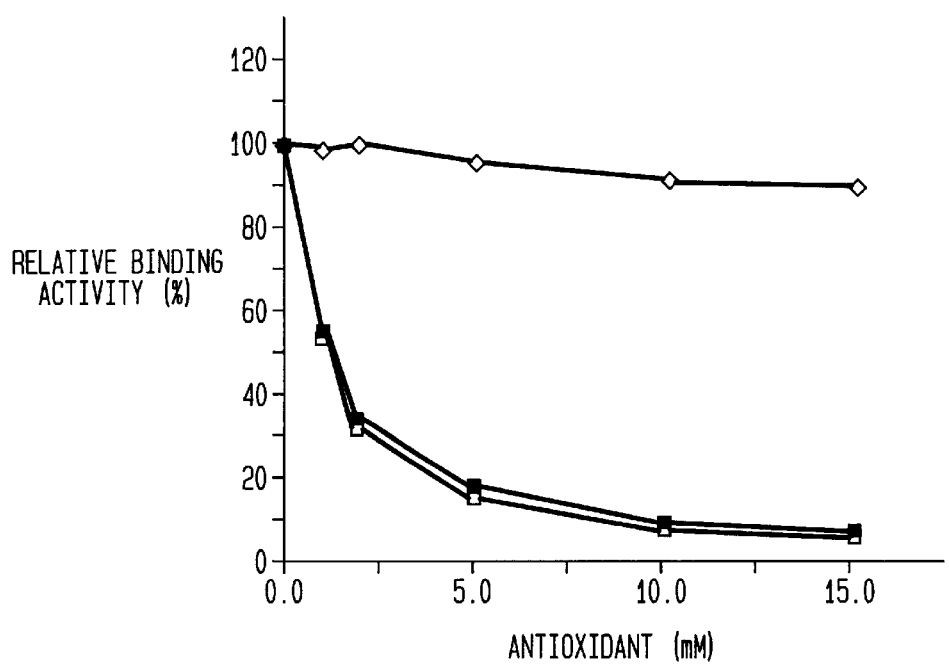
FIG. 5 is a graph of the effect on relative binding activity of native salicylic acid binding protein as a result of exposure to antioxidants where (□) represents beta-mercaptoethanol, (■) represents dithiothreitol, and (◊) represents ascorbic acid.

As shown in FIG. 5, the activity of the salicylic acid binding protein is affected by reducing agents betamercaptoethanol and dithiothreitol. On the other hand, the antioxidant ascorbic acid had little inhibitory effect on salicylic acid binding protein. This was measured in buffers containing 20 mM citrate, 5 mM MgCl and 10% glycerol pH 6.5 in addition to the indicated concentrations of antioxidant.

It is possible to further purify the native salicylic acid binding protein of the present invention. This is accomplished by subjecting the second eluent to subsequent chromatographic steps. For example, chromatographically fractionating the fractions containing the highest levels (peak) of salicylic acid binding activity from second eluent can be accomplished using a third gel filtration column. This will yield a third eluent. One type of third gel filtration column which may be used to chromatographically fraction the second eluent is an FPLC superose 6 column. FPLC, which stands for fast protein liquid chromatography, has found widespread application in protein purification because of its fast speed and high resolution. In accordance with the present invention, peak fractions from the second eluent of the prior gel filtration can be loaded onto an FPLC superose column which has been equilibrated with the buffer previously used. The samples can then be eluted with the same buffer, and the collected fractions can then be assayed again for both protein content and salicylic acid binding activity.

Thereafter, the peak fractions from third eluent is pooled and further fractionated chromatographically by the use of a fourth cation exchange column. A cation exchange column in accordance with the present invention can be, for example, a heparin sepharose column. In this case, peak fractions from the third element can be loaded onto a heparin sepharose column which is equilibrated with the buffer previously used. The column is washed extensively with the same buffer and is then eluted with the buffer containing a linear gradient of 0–1M KCl. The fractions are then again assayed for both protein and salicylic acid binding activity. Alternative approaches useful for the same purpose may include chromatography with, for example, affinity chromatography with immobilized nucleotide ligand (e.g. adenine 2, 5 diphosphate).

An additional separation step may be employed using a fifth gel filtration column. This column may be, for example, an FPLC superose 6 column as previously used in the third gel filtration column. The chromatographic conditions used in that instant are the same as previously described. Alternative gel filtration columns include those previously described with regard to the second and third separation steps.

After the fifth separation step, the fifth eluent is collected and analyzed using SDS-PAGE procedures.

SDS-PAGE, which stands for sodium dodecyl sulfatepolyacrylamide gel electrophoresis, is an excellent method to identify and monitor proteins during purification and to access the homogeneity of purified fractions. In addition, SDS-PAGE is routinely used for the estimation of protein's subunit molecular weights and for determining the subunit composition of purified proteins. SDS-polyacrylamide gel is prepared and run according to U. K. Laemmli, *Nature* (London) (1970), 680.

Figure 1:
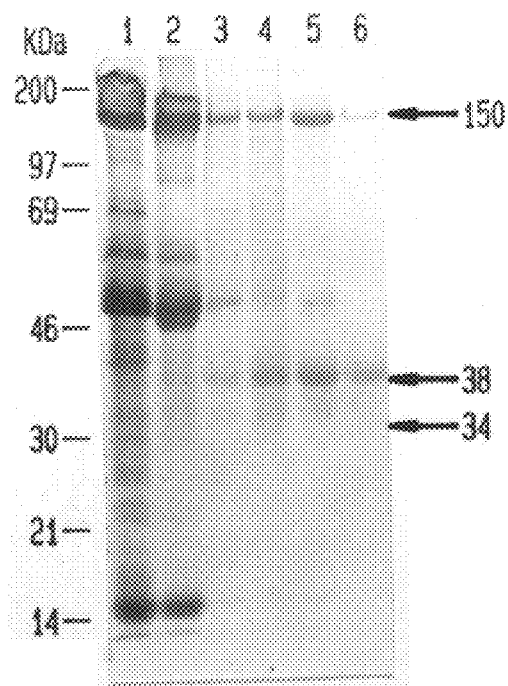
FIG. 1 is a photograph of an SDS-PAGE gel visualized with Coomassie Blue illustrating protein samples resulting from a five step separation procedure in accordance with one aspect of the present invention.

As a result of the SDS-PAGE analysis, three significant proteins were identified. One of the proteins identified had an apparent molecular weight of approximately 150 kDa. Other proteins had an apparent molecular weight of 34 kDa, and 38 kDa respectively. See FIG. 1 which is a SDS-PAGE gel as prepared by the procedures of Example 7. Lane 1 is the crude extract (180 μg of total protein loaded), lane 2 is pooled peak fractions of the DEAE-cellulose eluent (100 μg of total protein loaded), lane 3 is pooled peak fractions of the sephacryl 5–300 eluent (20 μg of total protein loaded), lane 4 is the superose 6 HR 10/30 eluent (20 μg of total protein loaded), lane 5 is pooled peak fractions of the heparinsepharose eluent (20 μg of total protein loaded), and lane 6 is a second sepharose 6 HR 10/30 eluent (10 μg of total protein loaded).

Figure 2A:
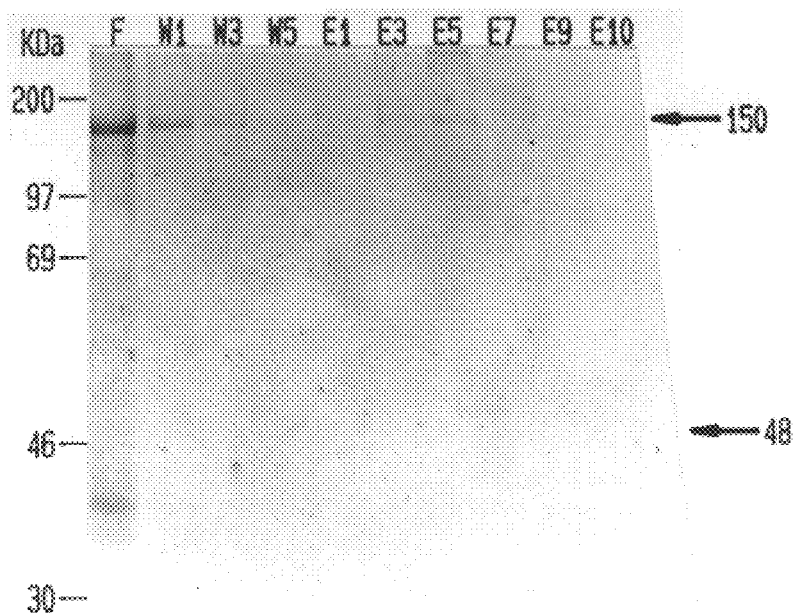
FIG. 2A is a photograph of an SDS-PAGE gel visualized with Coomassie Blue of protein sample fractions resulting from a four step separation process utilizing an immobilized reactive dye column in accordance with the present invention.
Figure 2B:
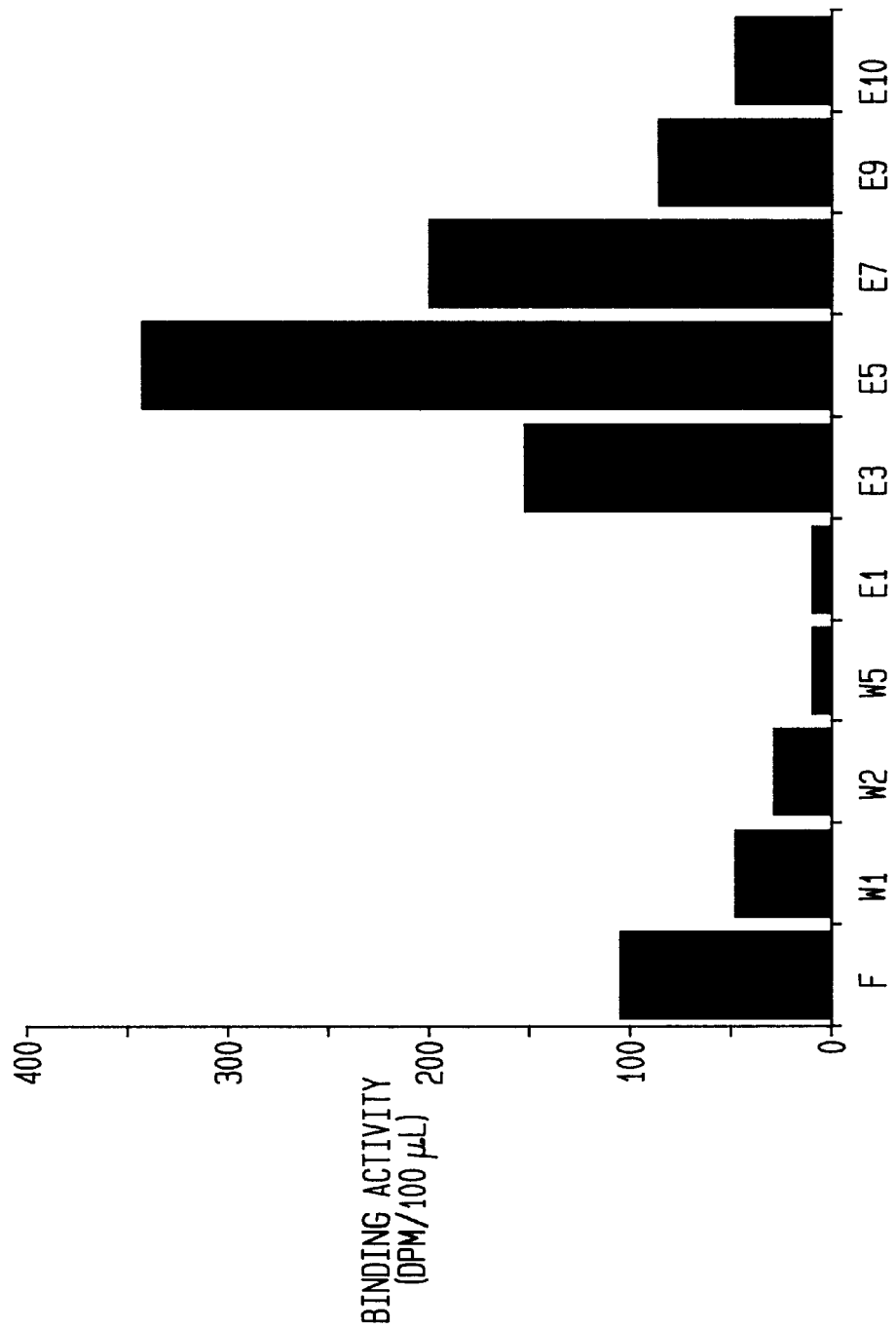
FIG. 2B is a salicylic acid binding activity profile of the fractions illustrated in FIG. 2A.

A preferred alternative separation method as exemplified in Example 9 eliminates the fourth cation exchange column in favor of an immobilized reactive dye column such as, a blue-dextran column. A higher concentration of binding activity, i.e. a higher concentration of protein exhibiting the ability to bind salicylic acid compounds per mg of protein was realized using this methodology. SDS-PAGE analysis of fractions eluted from the blue-dextran column indicate that at least two prominent proteins are found in the fractions with highest salicylic acid binding activity. One protein identified had an apparent molecular weight of approximately 150 kDa. The second prominent protein had, an apparent molecular weight of 48 kDa. See FIG. 2A which is an SDS-PAGE gel prepared by the procedure shown in Example 7 of the fourth column purification step of the four step purification protocol described above using a bluedextran immobilized reactive dye column. See also FIG. 2B which shows the salicylic acid binding protein activity profile of the eluent from the blue-dextran column.

Isolation of the gene encoding salicylic acid binding protein can be achieved using standard molecular biology techniques known to those of ordinary skill in the fields of biochemistry and molecular biology. One technique calls for the use of high affinity, mono specific polyclonal or monoclonal antibodies generated against salicylic acid binding protein. These antibodies can be used to screen λgt1 expression libraries from, for example, tobacco. This cDNA library and these antibody screening techniques have previously been used to isolate members of two families of PR genes from it (PR1a-c, J. R. Cutt et al., *Virology* "Disease response to tobacco mosaic virus in transgenic tobacco plants that constitutively express the pathogenesis-related protein PR1b" 173 (1989) 89–97; PR2c, Cote et al., "The pathogenesis-related acidic B-1,3-glucanase genes of tobacco are regulated by both stress and development signals" *Mol. Plant-Microbe Interactions* 4 (1991) 173–181).

A library was made from TMV-infected tobacco plants. To rule out the unlikely possibility that TMV infection might repress salicylic acid binding protein gene expression leading to the absence of its cDNA clone in the infected plant library, it has been shown that TMV infection neither represses nor induces salicylic acid binding activity. Additional libraries are available from Eric Lam at the Waksman Institute and Stratagene Cat. No. 936002.

An alternative to the use of antibodies to screen expression libraries is the use of mixed oligonucleotide probes (based on the protein sequence) as primers for polymerase chain reaction (PCR) generation of a cDNA probe (eg. J. A. Cassill et al., "Isolation of Drosophila genes encoding G protein-coupled receptor kinases", Proc. Natl. Acad. Sci. USA 88: (1991) 11067–11070). A partial amino-terminal sequence determination can be made directly on the salicylic acid binding protein purified to homogeneity, providing the N-terminus is not blocked. If the N-t is blocked, salicylic acid binding protein will be cleaved with a sequence specific protease (eg. trypsin), the peptides separated by HPLC, and then one of the larger and best separated peptides sequenced.

Another approach is applicable where the salicylic acid binding protein is only partially pure but the protein responsible for binding salicylic acid identified (perhaps using anti salicylic acid binding protein antibodies or by affinity labeling), then the mixture can be further fractionated by SDS-PAGE. The fractionated polypeptides will be transferred to polyvinylidene difluoride (PVDF) membranes, visualized by staining with coomassie brilliant blue, and the region of membrane containing salicylic acid binding protein subjected to N-t gas-phase sequencing (T. E. Kennedy et al., "Sequencing proteins from acrylamide gels" Nature 336: (1988) 499–500). Because of the excellent sensitivity of gas-phase sequencing (10–100 pmoles), obtaining sufficient quantities of salicylic acid binding protein will not be a problem (note salicylic acid binding protein is relatively abundant at 5 pmoles/μg of soluble protein). Sequencing can be conducted by the Protein Microchemistry Laboratory, a Network Service Laboratory of the N. J. CABM. See generally the procedures discussed in V. Cleghon and D. F. Klessig, "Characterization of the adenovirus DNA-binding protein's nucleic acid binding region by partial proteoloysis and photochemical cross-linking", J. Biol. Chem., September 1992.

Based on the amino acid sequence, two sets of mixed (degenerate) primers (18–26 bases in length that correspond to the amino acid sequence) can be made corresponding to the N-t(5') and reverse complement of the most C-t sequenced portion (3') of the polypeptide/protein. Each primer will have a restriction enzyme recognition site (EcoRI or SaII for 5' primer and Hind III for 3' primer) plus a GGGC clamp or extension (for efficient cleavage of the restriction site) for efficient, directional cloning into a pUC based sequencing vector such as pUC118/119. Either reverse transcribed RNA from tobacco or the cDNA from the λgt11 libraries could be used as the PCR templates. The previously described cDNA libraries can be employed using any one of a number of recently published protocols (eg. S. M. Beverly, "Enzymatic Amplification of DNA by the Polymerase Chain Reaction", In Current Protocols in Molecular Biology, Wiley and Sons, New York, (1991) pp. 15.4.1–15.4.6; S. J. Scharf, "Cloning with PCR" In PCR Protocols, Academic Press, New York, (1990) pp. 84–91; G. H. Keller, "Probe and Target Amplification Systems" In DNA Probes, Macmillan Publishers, United Kingdom, (1989) pp. 215–231; J. A. Cassill et al., "Isolation of Drosophila genes encoding G protein-coupled receptor kinases" Proc. Natl. Acad. Sci. USA 88: (1991) 11067–11070).

The PCR products can be fractionated on acrylamide gels, and those, whose products correspond in length to the distance between the ends of the primers (60–180 bases depending on size of the sequenced region of the polypeptide), will be cloned. Individual clones will be sequenced, and any clone which matches the amino acid sequence will be used as a probe to screen the cDNA library using the standard closing procedure described in detail in the laboratory manual "Molecular Cloning" Second Edition, J. Sambrook, E. F. Fritsch and T. Maniatis 1989 Cold Spring Harbor Laboratory Press, the text of which is hereby incorporated by reference. Eventually a genomic library which is commercially available from Clontech Cat. No. FL1070d will be employed.

To increase the chances of identifying a PCR clone which matches the amino acid sequence a larger population of clones can be screened with an oligonucleotide probe corresponding to amino acid's internal to the sequenced segment of the polypeptide. A strategy of nested primers (Mullis and Faloona, "Specific synthesis of DNA in vitro via a polymerase catalyzed chain reaction" *Methods in Enzymology* 155 (1987) 335–350) can be used to increase the specificity of amplification. After amplifying a region of DNA with one set of primers, amplification can be continued with a second pair of primers that are closer together (providing the sequenced region of the polypeptide is sufficiently long). Any nonspecific amplification products directed by the first primer set are very unlikely to serve as a template for the second primer set.

The cDNA and/or genomic clones isolated as described above has been sequenced using the dideoxynucleotide-based sequenase version 2 DNA sequencing kit from U.S. Biochemical. cDNA or genomic clones encoding the salicylic acid binding protein can be transferred to plants rising a Ti based binary vector and utilizing the 35S promoter of Cauliflower Mosaic Virus for expression. A number of such vectors are available including pGA643. Using standard procedure for transformation of plant cells via cocultivation of *Agrobacterium tumefaciens* containing the binary vector with plant (tobacco) protoplasts, transgenic plants will be constructed. See G. An et al., "Binary vectors" In Plant Molecular Biology Manual Editors S. B. Geluh, R. A. Schilperoort, D. P. S. Verma Kluwer, Academic Publishers 1988 pg. A3/1–A3/19). Other promoters such as the 19S and nos could be used to control expression. Other DNA transformation procedures can be used to obtain transformed plants such as the "biolistics" or particle gum procedures known to the field. These procedures are particularly suitable for the transformation of monocotyledonous species. See I. Potrykus "Gene transfer to Plants: Assessment of Published Approaches and Results" *Ann. Rev. Plant Physiol. Plant Mol. Bid.*, 42 (1991) 205–225.

The inventors have shown that the cloned SABP gene sequence has high homology to catalase and also possesses catalase activity. The involvement of reactive oxygen species in host defense against microorganisms and the discovery that the SABP is a catalase suggest that the role of salicylic acid in defense may in fact be through its modulation of the abundance of reactive oxygen species via its influencing the activity of plant catalases. In the presence of salicylic acid the catalase activity of the highly purified SABP was inhibited by 80% (table 6). A similar level of inhibition of catalase activity by SA ($^-$70%) was also observed with crude extracts; inhibition appeared to be reversible since the catalase activity could be largely recovered by extensive dialysis. 2,6-dihydroxybenzoic acid and acetylsalicylic acid, both of which are active inducers of PR genes and resistance, were effective inhibitors of the catalase activity of SABP. Quantitatively 2,6-dihydroxybenzoic acid was somewhat stronger and acetylsalicylic acid was weaker than SA for inhibition of catalase. 2,3-dihydroxybenzoic acid, which has only weak biological activity, was a poor inhibitor while five structurally similar but biologically inactive analogues were ineffective in inhibiting the catalase activity. Moreover, the analogues' effectiveness in inhibiting SABP's catalase activity correlated with their ability to compete with [$^{14}$C]SA for binding to SABP, indicating that binding of SA and its analogues to SABP was responsible for the inhibition of the catalase activity.

Figure 16:
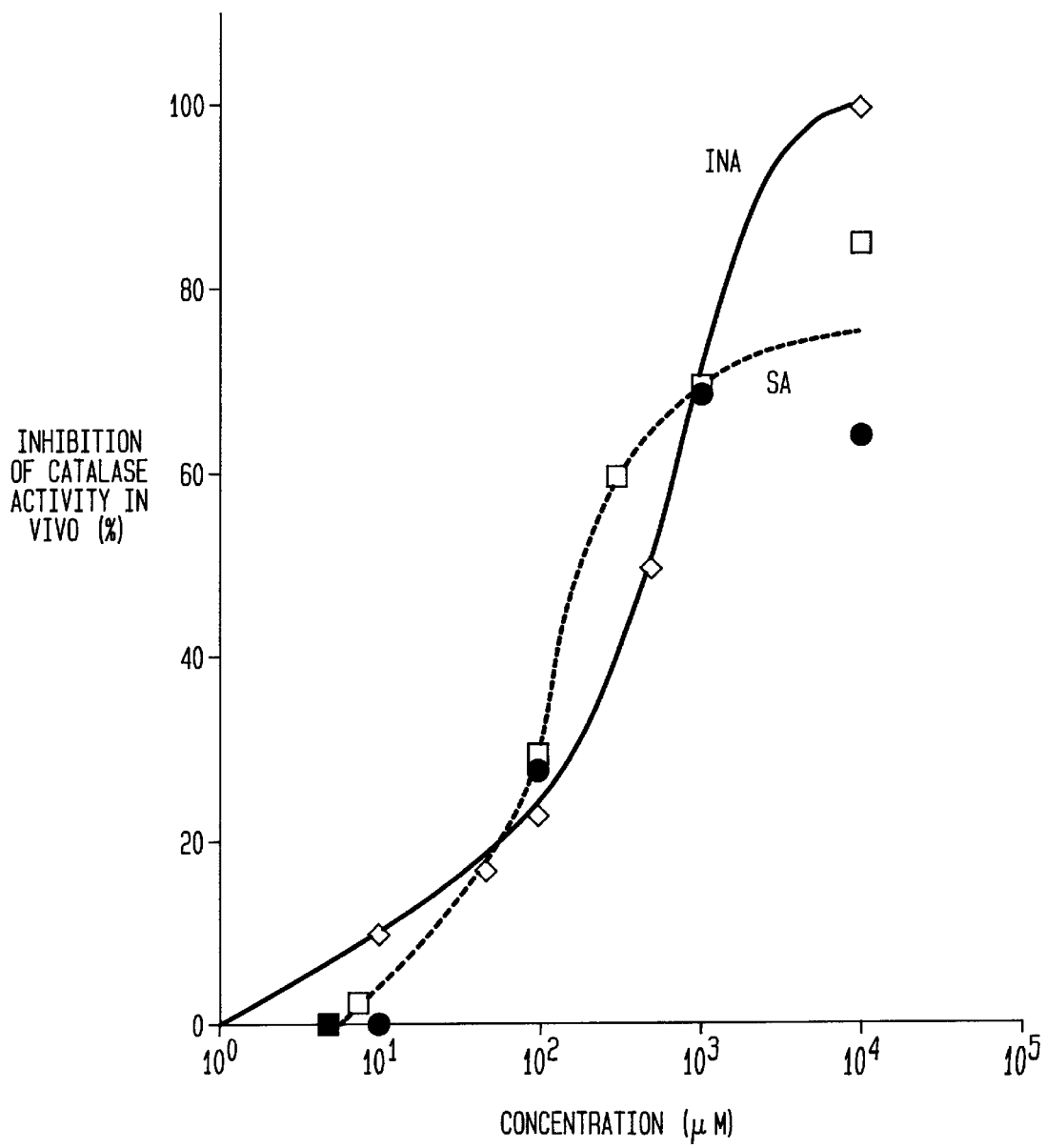
FIG. 16 is a dose response analysis of SA (●), (□) and INA (◇).

The inventors have also shown that INA, a further compound capable of inducing the systemic acquired resistance response in plants and expression of the same SAR genes as salicylic acid, operates by inhibiting SABP/catalase. INA does not, however, operate through salicylic acid as it does not induce an increase in the abundance of salicylic acid. Rather, it operates directly by inhibiting catalase activity. The inventors have found that the physiological mode of action of INA is different to most abiotic inducers of SAR gene expression (e.g. polyacrylic acid, thiamine-HCl, α-aminobutyric acid, and barium chloride) which they show to act through salicylic acid (Table 7). Using a tobacco cell suspension culture and an oxygen electrode to measure in vivo catalase activity by determining the rate of $H_2O_2$-dependent $O_2$ production immediately after the addition of $H_2O_2$ it was possible to demonstrate that SA and INA have similar dose response curves for catalase inhibition in vivo (FIG. 16).

TABLE 7

| Treatment | PR-1 gene activation | Reduction in lesion size (%) | SA/SAG (μg/g FW) |
|---|---|---|---|
| polyacrylic acid | + | 100 | 2.51 |
| thiamine-HCl | + | 71 | 1.50 |
| α-amino butyric acid | + | 63 | 2.06 |
| BaCl$_2$ | + | 60 | 2.77 |
| dichloro-isonicotinic acid (INA) | + | 72 | <0.05 |
| wounding | − | 0 | <0.05 |
| H$_2$O | − | 0 | <0.05 |

Furthermore, numerous analogues of INA were tested in this system. A close correlation was observed between the biological activity of the analogues and their ability to bind catalase and inhibit its activity, suggesting that inhibition of catalase was responsible for the biological activity of INA (see Table 8). Using the cell suspension described above, three chlorinated analogues of salicylic acid were identified which were potent inducers of PR-1 gene expression and enhanced resistance to TMV infection. They were also more effective than salicylic acid in inhibiting catalase activity (see Table 8).

Furthermore, the inventors have shown that the abundance of $H_2O_2$ increased in SA- or 3-amino-1,2,4-triazole (3AT; a specific inhibitor of plant and animal catalases) treated tobacco leaves by 50–60% over the control levels observed in water-treated leaves. By contrast, 3-hydroxybenzoic acid was unable to enhance the in vivo abundance of $H_2O_2$, consistent with its ineffectiveness in both binding SABP and inhibiting catalase activity. Thus, elevated levels of $H_2O_2$, and in turn, enhanced oxidative stress in vivo, were consistent with inhibition of catalase activity by SA observed in vitro.

In addition, the injection of $H_2O_2$ or the catalase inhibitor 3AT into tobacco leaves was found to induce the expression of PR-1; the induction of PR-1 parallels the well documented induction by salicylic acid. PR-1 gene expression was also induced by treating tobacco leaves with glycolate (an intermediate in photorespiration which serves as a substrate for the generation of $H_2O_2$ by glycolate oxidase present in leaves) and with paraquat (a herbicide which can be reduced in vivo and subsequently reoxidized by transfer of its electrons to oxygen to form superoxide anion; superoxide can be converted either spontaneously or enzymatically by superoxide dismutase to $H_2O_2$). Thus, the SA signal appears to be propagated through $H_2O_2$ which may act as a secondary messenger, to activate defense-related PR genes.

Because salicylic acid binding protein's role in defense may be through its modulation of the abundance of reactive oxygen species, it is likely that the expression of the SABP gene in transgenic plants in antisense orientation so as to reduce the abundance of native SABP may be advantageous. Standard procedures for the production of appropriate constructions and their transformation into transgenic plants have been used for this. Transgenic tobacco plants expressing the SABP/catalase gene of this invention in antisense orientation were found to have reduced abundance of both low molecular weight (LMW) and high molecular weight (HMW) forms of catalase. Although the LMW form was typically eliminated entirely, the HMW form was eliminated to various degrees in different transgenic lines, presumably reflecting its lower homology to the expressed antisense transgene. Analysis of transgenic lines revealed there to be a direct correlation between inhibition of catalase activity and induced expression of PR-1 and enhanced resistance to TMV.

It has also been shown that compounds including salicylic acid and INA, in addition to inhibiting catalase activity, also inhibit the activity of ascorbate peroxidase. See Table 9.

TABLE 9

| | Control | 100 μM SA | | 1,000 μM SA | | 100 μM INA | | 1,000 μM INA | |
|---|---|---|---|---|---|---|---|---|---|
| Enzyme[a] | Activity[b] | Activity | Inhibition | Activity | Inhibition | Activity | Inhibition | Activity | Inhibition |
| APX | 4.9 ± 0.2 | 2.0 ± 0.2 | 59% | 0.24 ± 0.1 | 95% | 2.25 ± 0.4 | 54% | 0.24 ± 0.2 | 95% |
| POX | 2.8 ± 0.5 | 2.7 ± 0.3 | 3% | 2.7 ± 0.4 | 3% | 2.8 ± 0.4 | 0% | 2.7 ± 0.4 | 3% |
| HRP | 240 ± 2 | 251 ± 11 | −4% | 237 ± 21 | 1% | 236 ± 8 | 1% | 242 ± 16 | 0% |

[a]APX, ascorbate peroxidase; POX, guaiacol peroxidases; HRP, horseradish peroxidase.
[b]Oxidation of ascorbate by ascorbate peroxidase and guaiacol by guaiacol peroxidases (and horseradish peroxidase) was assayed as described in Example 30. Enzyme activities are given as μmols of oxidized substrate min$^{-1}$ mg$^{-1}$ protein. Assays were done in triplicate.

Salicylic acid and INA do not inhibit a second class of peroxidases, called guaiacol peroxidases. Guaiacol peroxidases (which includes horseradish peroxidase) use guaiacol rather than ascorbate as a major substrate. Ascorbate peroxidase, but not guaiacol peroxidases, plays a major role in scavenging (destroying) of intracellular $H_2O_2$ (Asada, Physiologia Planatarum 85: 235 (1992): Asada, in "Causes of Photooxidation Stress and Amelioration of Defense Systems in Plants," eds. C. H. Foyer and P. M. Mullineaux, CRC Press, Boca Raton, pp. 78–106 (1994)). Using protein extracts prepared from tobacco leaf tissue and spectrophotometric methods described by Nakano and Asada (Plant Cell Physiol. 22: 867 (1981)) for ascorbate peroxidase activity measurements or by Chance and Maehly, (Methods Enzymol. 2: 764 (1955)) for guaiacol peroxidases activity measurements, inhibition by salicylic acid and by INA of ascorbate peroxidase activity, but not of guaiacol peroxidases activity was demonstrated.

Figure 17:
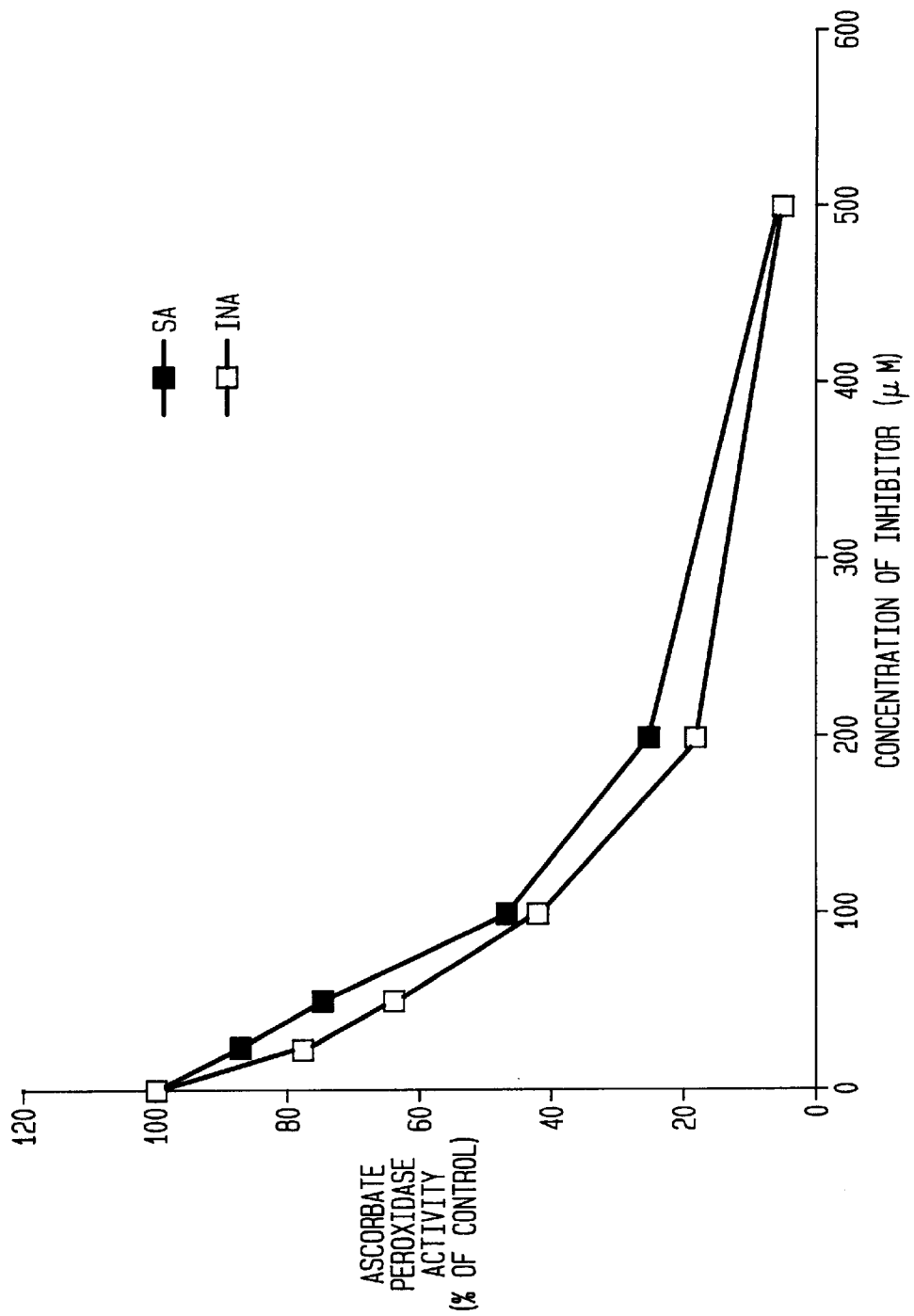
FIG. 17 illustrates the concentration dependent inhibition of ascorbate peroxidase from tobacco by SA and INA.

To estimate the concentration of SA or INA necessary for 50% inhibition ($I_{50}$), ascorbate peroxidase activity was measured in the presence of 750 $\mu$M ascorbate and different concentrations of SA or INA (25 to 500 $\mu$M; FIG. 17). 50% inhibition was obtained at approximately 80 $\mu$M salicylic acid and at 95 $\mu$M INA.

Furthermore, numerous analogues of salicylic acid were tested for their effect on ascorbate peroxidase in this system. As illustrated in Table 10, a close correlation was observed between the biological activity of the analogous and their ability to inhibit ascorbate peroxidase. See Table 10.

TABLE 10

| SA and Analogues | Biological Activity[a] | % Inhibition[b] |
| --- | --- | --- |
| Salicylic acid (SA) | + | 83 ± 9 |
| 4-Chlorosalicylic acid | + | 58 ± 4 |
| 5-Chlorosalicylic acid | + | 73 ± 5 |
| 3,5-Dichlorosalicylic acid | + | 59 ± 5 |
| 2,6-Dihydroxybenzoic acid | + | 72 ± 8 |
| 3-Hydroxybenzoic acid | − | 28 ± 7 |
| 4-Hydroxybenzoic acid | − | 0 ± 6 |
| Thiosalicylic acid | − | 0 ± 2 |
| 4-Aminosalicylic acid | − | 9 ± 5 |

[a]Biological activity is based on results of White, Virology, 99:410 (1979), van Loon Neth. J. Plant Pathol., 89:265 (1983), Abad et al. Antiviral Res., 9:315 (1988), Doherty et al., Physiol Mol. Plant Pathol., 33:377 (1988) and Conrath et al., Proc. Natl. Acad. Sci. USA, in Press. (1995).
[b]Ascorbate peroxidase was assayed in presence of 200 $\mu$M of the various compounds, which have been added from stock solutions (10 mM in water, adjusted to pH 5.8 with KOH). Values represent results from several independent preparations, each assayed in triplicate. The specific activity of the control was between 4.1 and 5.8 $\mu$mol oxidized ascorbate $min^{-1}mg^{-1}$. Several of the analogues showed significant quenching of auto oxidation of ascorbate in the absence of enzyme. Therefore, all of the % inhibition values presented have been corrected for this quenching.

EXAMPLE 1

Plant tissues (200 g) (leaves of tobacco) were sliced and then homogenized with a polytron homogenizer in one liter of a homogenization buffer containing 20 mM citrate (pH 6.5), 5 mM $MgCl_2$, 10% glycerol, 30 $\mu$g/ml polyvinylpolypyrrolidone. The homogenate was filtered through four layers of cheesecloth and then centrifuged four minutes at 40,000 g at 4° C. in an Eppendorf microcentrifuge.

EXAMPLE 2

The resulting supernatant from Example 1 was loaded onto a DEAE-Sephacel column (2.5×15 cm; purchased from Pharmacia LKB, Piscataway N.J.) that had been equilibrated with the aforementioned homogenization buffer without polyvinylpolypyrrolidone (Buffer A). The column was washed extensively with Buffer A, and the salicylic acid binding protein was then eluted with 300 ml of Buffer A containing a linear gradient of 0–0.5M KCl. The peak fractions with the highest salicylic acid binding activity (peak fractions) were pooled, concentrated with $N_2$-aided filtration concentrator (purchased from Millipore, Bedford, Mass.) and loaded onto a Sephacryl S-300 gel filtration column (2.5×100 cm; purchased from Pharmacia, Piscataway, N.J.). The salicylic acid binding protein was eluted with the Buffer A at the flow rate of 40 ml/hr. The peak fractions (8 ml/fraction) from the gel filtration column were then pooled and used for further characterization. In addition to purification, this gel filtration chromatography was used to estimate the molecular weight of the salicylic acid binding protein.

EXAMPLE 3

Apparent average native molecular weight was determined as follows: the bed volume ($V_b$) was directly calculated from the column dimensions and the void volume ($V_v$) was determined using blue-dextran (Pharmacia). The elution volumes ($V_e$) of the following molecular weight ($M_r$) standards were also measured: thyroglobulin ($M_r$-669 kDa); ferritin ($M_r$-440 kDa); catalase ($M_r$-230 kDa); aldolase ($M_r$-158 kDa); albumin ($M_r$-67 kDa) and ovalbumin ($M_r$ 43 kDa). A calibration curve was obtained by plotting the Kav value $[(V_e-V_v)/(V_b-V_v)]$ against the log $M_r$ of each standard. The molecular weight of the salicylic acid binding activity was then estimated by fitting its elution volume to the calibration curve using linear regression procedure.

EXAMPLE 4

The pooled peak fractions from the first sephacryl S-300 gel filtration column were loaded onto a superose 6 HR10/30 column (which is operated by an FPLC system; purchased from Pharmacia, Piscataway, N.J.). Because of the large volume of the pooled fractions from the sephacryl S-300 column, the fractionation by FPLC on the superose 6 column had to be repeated many times (approximately 20) using 0.5 ml for each injection. Buffer A is used here for both equilibration and elution. The flow rate used is 0.35 ml/min. The protein concentration of each fraction (0.35 ml) was monitored by a UV detector at 280 nm and the binding activity was determined with spin-column chromatography as described in Example 8.

EXAMPLE 5

Fractions with peak activity resulting from Example 4 were then pooled and loaded onto a heparin-sepharose mini-column (2 ml; in Bio-Rad poly-prep mini column purchased from Pharmacia, Piscataway, N.J.), which was equilibrated with Buffer A. After loading the sample, the column was extensively washed with the Buffer A, and the salicylic acid binding protein was eluted with 30 ml of the Buffer A containing a linear gradient of 0–1M KCl. The peak fractions was identified by directly assaying for the salicylic acid binding activity using the spin-column exclusion chromatography.

EXAMPLE 6

The peak fractions from Example 5 were then pooled and subjected to another superose 6 HR 10/30 gel filtration column operated by an FPLC system as previously described. Gel filtration was extensively used because most green plant tissue contains very large amounts of soluble ribulose bisphosphate carboxylase/oxygenase which is a major contaminant during the purification but has a large molecular weight (approximately 550 kDa) that facilitates its separation from salicylic acid binding protein by gel filtration. SDS-PAGE was then used to identify the significant protein species still present in the peak fractions from the second FPLC gel filtration chromatography.

EXAMPLE 7

Polyacrylamide gels (7–15%) was prepared by copolymerization of acrylamide with N,N'-methylenebisacrylamide using standard protocols. Samples for SDS-PAGE were prepared by mixing the protein sample with gel loading buffer containing both SDS (1%) and reducing agent β-mercaptoethanol (100 mM) (or 50 mM DTT) to break possible disulfide bonds present in proteins. Gels were run at constant voltage (50V for stacking gel portions and 100V for resolving gel), and the proteins on the gel were visualized by either Coomassie blue or silver staining.

EXAMPLE 8

A key element during the characterization and the purification process is a simple, inexpensive, sensitive and reliable method for determining the salicylic acid binding activity. For this purpose, spin-column exclusion chromatography was used to separate the bound [$^{14}$C] salicylic acid (excluded) from the bulk free salicylic acid (included). Specifically, a 1.5 ml Eppendorf tube was punctured at the tip with a 20-gauge needle and a small amount of glass wool was added to cover the small hole. The tube was then filled with Bio-Gel P-6DG desalting gel (exclusion limit 6 KDa; purchased from Bio-Rad, Melville, N.Y.) which have been swollen in water. An alternative gel is Sephadex G-25 fine (from Pharmacia, Piscataway, N.J.). Excess liquid in the gel was removed and centrifuged for 5 minutes at full speed in a Dynamic centrifuge (Becton Dickinson). The process was then repeated several times until the gel filled the tube. After incubation of an aliquot of the extract or column fractions for 2 hr at 4° C. with 5 $\mu$M–20 $\mu$M [$^{14}$C salicylic acid] (specifically radioactivity 55 Ci/mol; purchased from New England Nuclear), 150 $\mu$l of proteins binding sample was loaded onto the tube column, which was then rapidly centrifuged for 2 minutes at full speed and the solution of proteins and bound [$^{14}$C-salicylic acid] that was excluded from the gel was collected into another tube that had been placed under the tube column during the centrifugation. One hundred microliters of this solution was then used to determine the amount of bound salicylic acid. With this binding assay, characterization of the salicylic acid binding protein can be carried out very rapidly. For example, to determine the inhibitory effect of various salicylic acid analogues on salicylic acid binding activity, these individual analogues were included in the binding mixture containing both the protein and [$^{14}$C] salicylic acid during the 2 hr incubation, and resulting binding activity was determined in comparison to the activity in the absence of these analogues. Likewise, to determine the effect of pH and antioxidants on the binding activity the protein sample was either dialyzed against a large volume of buffers with different pH or antioxidants were added to the protein sample to various concentrations and the resulting binding activities were then determined with the spin-column method in comparison with the activity determined in the absence of these treatments.

EXAMPLE 9

The procedures used in Examples 1–4 above were repeated and fractions with peak activity resulting from Example 4 were pooled and loaded onto a blue-dextran agarose mini column (2.5 ml in Bio-Rad poly-prep mini column, purchased from Sigma Company, St. Louis, which has been equilibrated with buffer A. After loading the sample, the column was washed with the buffer A and the salicylic acid binding protein was eluted with 30 ml of the buffer A containing a linear gradient of 0–1.0 mM ATP and 0–1M Kcl. The peak fractions can be identified by directly assaying for the salicylic acid binding using the spin-column exclusion chromatography and the proteins of each fraction can be examined by polyacrylamide gel electrophoresis (shown in FIG. 2).

EXAMPLE 10

The level of PR1 protein in tobacco leaves was analyzed by immunoblot analysis to establish biological activity. Three leaf discs (1 cm in diameter) were homogenized in 200 microliters of buffer containing 50 mM Tris (pH 8.0), 1 mM EDTA, 12 mM beta-mercaptoethanol and 10 mg/ml phenylmethylsulfonyl fluoride. The homogenate was centrifuged at full speed for 10 minutes in an Eppendorf microcentrifuge. The supernatant was fractionated with 15% polyacrylamide gel under denatured conditions. Protein blotting was done with a monoclonal antibody specific to PR1 protein and protein-antibody complexes were detected with an ECL kit from Amersham.

EXAMPLES 11–15

Originally, the inventors believed that tobacco derived salicylic acid binding protein had an apparent average native molecular weight of about 180 kDa. They have subsequently shown, however, that in fact the apparent average native molecular weight of tobacco derived salicylic acid binding protein, as determined by gel filtration, is approximately 240 kDa. This was confirmed by SDS-PAGE procedures from which an apparent molecular weight of 280 kDa was determined. The 40 kDa difference in molecular weight between the two procedures is insignificant and results from the inherent differences between the two weight determination procedures.

The difference between the originally determined 180 kDa value of the apparent average native molecular weight and the subsequently determined 240 kDa, value appears to be based upon the salt concentration used during gel filtration chromatography. When lower salt concentration buffers were used, as exemplified in Examples 2, 4, and 6, it appears that the salicylic acid binding protein has some weak, nonspecific interaction (binding) to the gel matrix. This slows the movement of the protein through the gel. When the salt content of the buffer used was elevated by a 100 mM KCl supplement, as exemplified by Example 11, the nonspecific binding of the protein to the matrix was, apparently, suppressed. This led to a more accurate determination of salicylic acid binding protein's apparent average native molecular weight of approximately 240 kDa.

What follows is the discussion of the modified purification protocol used to obtain the 240 kDa molecular weight determination and a discussion of the subsequent characterization steps taken by the inventors.

EXAMPLE 11

Modified Purification Scheme

As reported in Examples 1–10, two "low salt" concentration purification schemes were initially utilized in accordance with the present invention. The first purification scheme employed the methods utilized in Examples 1, 2, 4, 5 and 6, in that order. The second purification scheme employed the techniques described in Examples 1, 2, 4 and 9, also in that order. Subsequently, a new purification procedure was developed which roughly corresponded to the use of the separation steps described in Examples 1, 2, and 4, in that order. This purification protocol resulted in the realization of the 240 kDa molecular weight determination.

The only modifications to Example 2 was the addition of 100 mM KCl to Buffer A during gel filtration chromatography on sephacryl S-300. The next step in purification used the procedures described in Example 9 with the modification that the salicylic acid binding activity was step eluted with Buffer A supplemented with 0.7M KCl. This replaced elution with a linear gradient of 0–10 mM ATP and 0–1M KCl as previously described. The final purification step corresponding to previous Example 4, was also modified. However, the only difference in this step involved the use of a Buffer A supplemented with 100 mM KCl.

Specifically, crude homogenate was prepared from leaves of tobacco as described in Example 1 except that 1 mM EDTA ([ethylene dinitrilo]-tetraacetic acid) was added to the homogenization buffer; all subsequent buffers also contained 1 mM EDTA. The filtered and clarified (centrifuged) homogenate was then subjected to ion exchange chromatography on DEAE-sephacel and then to gel filtration chromatography on sephacryl S-300 as described in Example 2 with the modification that Buffer A was supplemented with 100 mM KCl during gel filtration chromatography.

The pooled peak fractions from the sephacryl S-300 gel filtration column were pooled and concentrated 5 fold with a Whatman ultra filtration apparatus using a YM-30 membrane. The concentrated protein was chromatographed on a blue-dextran agarose column as described in Example 9 except that the salicylic acid binding activity was step eluted with Buffer A supplemented with 0.7M KCl rather than using a linear gradient of 0–10 mM ATP and 0–1M KCl.

The pooled peak fractions from the blue-dextran agarose column were chromatographed on a superose 6 HR 10/30 column as described in Example 4 with the modification that Buffer A was supplemented with 100 mM KCl.

Figures 7A, 7B:
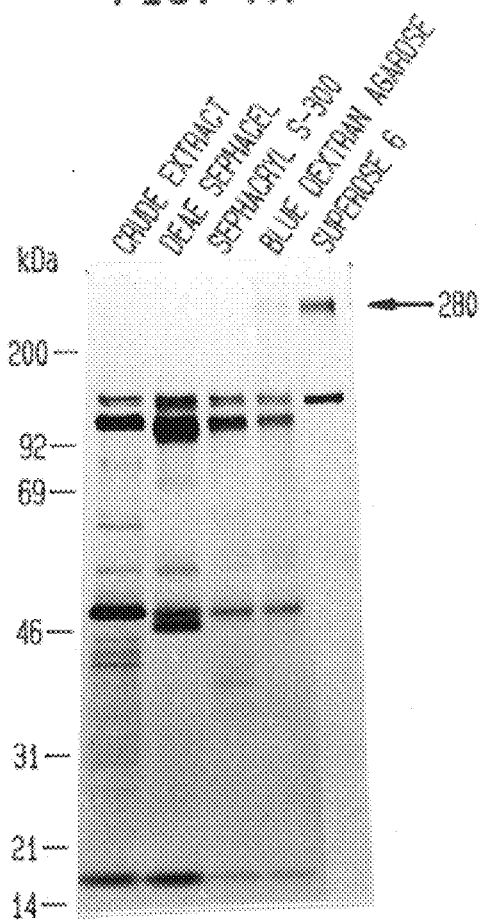
FIG. 7 relates to the purification of salicylic acid binding protein from tobacco leaves having an apparent molecular weight of 280 kDa by SDS-PAGE.

A small sample of the pooled peak fractions for each chromatography step was analyzed by SDS-PAGE as described in Example 7 and the results are shown in FIG. 7. FIG. 7A is the SDS-PAGE (7.5–15%) of protein samples from a crude extract (homogenate) and the peak fractions from the four chromatography steps including DEAE sephacel, sephacryl S-300, blue-dextran agarose and superose 6 described in this example. This illustrates the elution profiles of the salicylic acid binding protein. Molecular shown of marker proteins are shown on the left side. The 280 kDa protein that copurified with salicylic acid binding activity is indicated on the right side. The gel was silver stained.

FIG. 7B tabularizes the recovery of proteins and salicylic acid binding activity during purification of salicylic acid binding protein. The four chromatography steps described above resulted in a reduction of total protein by a factor of 1570 and a 250-fold increase in specific binding activity.

FIG. 8 illustrates the elution profiles of proteins and salicylic acid binding activity on blue-dextran agarose (FIGS. 8A and 8C) and superose 6 (FIGS. 8B and 8D) columns. Active fractions from the sephacryl S-300 column were pooled and applied to a blue-dextran agarose column. After extensive washing, the bound salicylic acid binding activity was eluted with the loading and washing buffer (Buffer A) containing 0.7M KCl (FIG. 8A). Various flow-through and eluted fractions were subject to SDS-PAGE (7.5–15%) analysis. A 280 kDa protein was highly enriched in fractions 72–76 (FIG. 8C) which also contained the highest levels of salicylic acid binding activity (FIG. 8A). The active fractions from the blue-dextran agarose column were then combined and applied to a superose 6 HR 10/30 column using a FPLC system (FIG. 8B). The eluted fractions were again subjected to SDS-PAGE analysis (FIG. 8D). The 280 kDa protein was found to co-elute with the salicylic acid binding activity, i.e. fractions 40–44 (FIG. 8B). Fraction numbers from the columns are indicated on top of the silver stained gels (FIG. 8C and FIG. 8D). A 280 kDa protein species copurified with the salicylic acid binding activity (indicated by arrows in FIGS. 7 and 8).

Figure 8A:
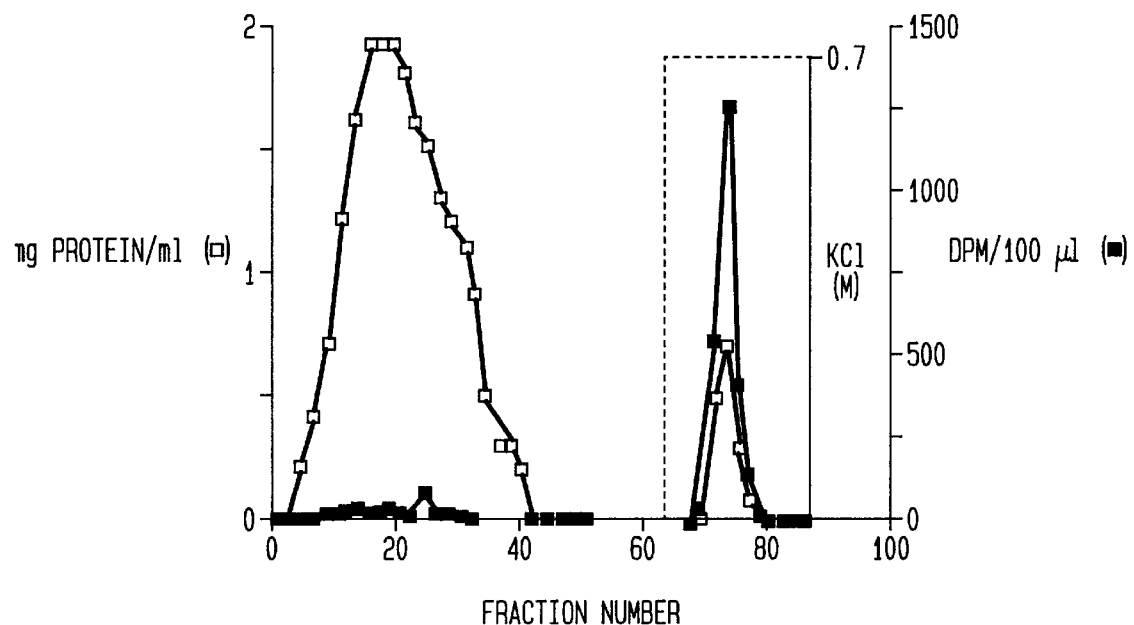
FIG. 8 illustrates the elution profiles of proteins and of salicylic acid binding activity of a partially purified protein mixture on blue-dextran agarose and superose 6 columns.
Figure 8B:
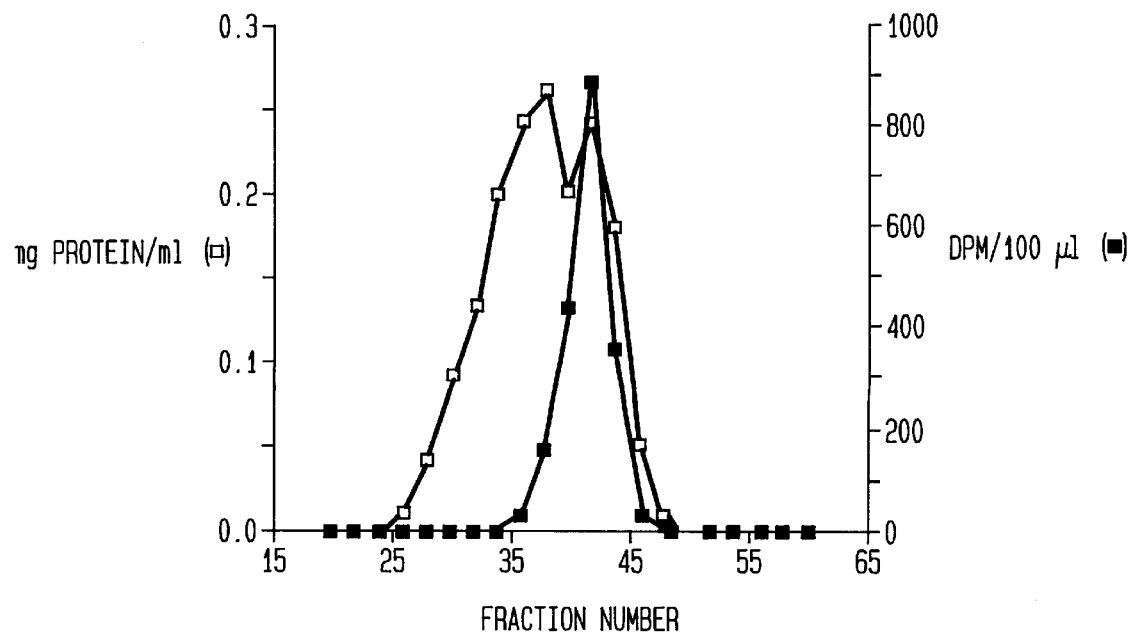
Figure 8C:
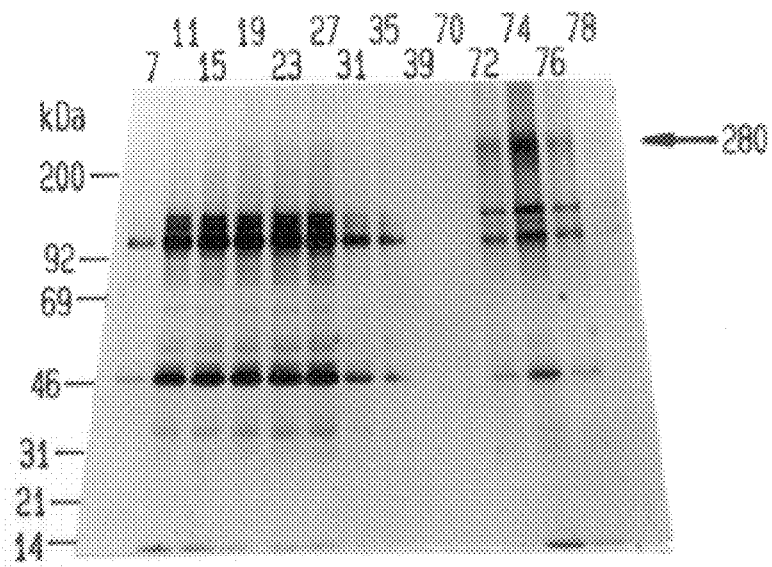
Figure 8D:
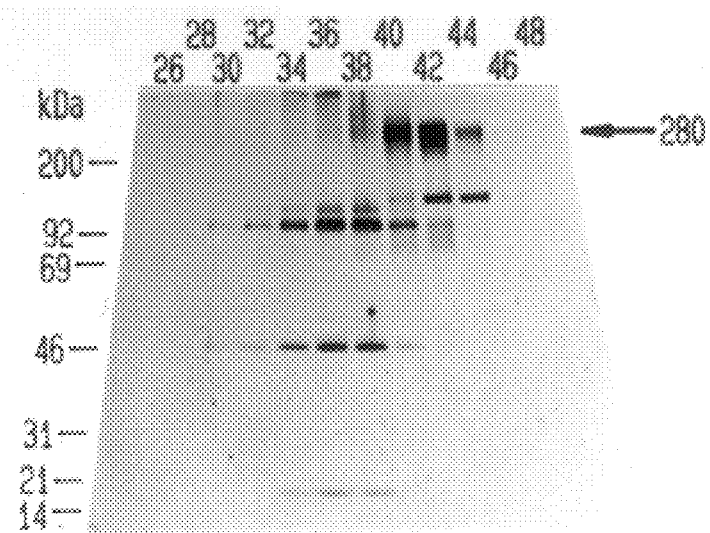

The result of the modified purification scheme described herein is a highly purified mixture of a limited number of proteins. As shown in FIG. 7A, under the right hand most column identified by the legend "superose 6", two bands are prevalent. The band at the top indicated by the arrow has an apparent molecular weight of 280 kDa. A second band located below it, having an apparent molecular weight of about 150 kDa, is also apparent. FIG. 8 illustrates that in its final two steps of purification (i.e. blue-dextran agarose and superose 6 chromatography) the 280 kDa protein and the salicylic acid binding activity co-elute. In other words, the fractions with the highest levels of salicylic acid binding activity (eg. fraction 74 in FIG. 8A and fraction 42 in FIG. 8B) also had the highest amounts of the 280 kDa protein (FIG. 8C and 8D). In contrast, while 150 kDa species also appeared to co-elute with the salicylic acid binding activity, the correspondence between levels of binding activity and amounts of 150 kDa protein were not as compelling. Thus, while the two prevalent proteins contained within the purified protein mixture obtained by the practice of Example 11 are a 280 kDa and a 150 kDa protein, respectively, the inventors suspected that the 280 kDa protein is salicylic acid binding protein. To validate that suspicion, the tests described in Examples 12–15 were performed.

Briefly, the purified protein mixture, including the two prevalent proteins and a number of other less abundant proteins resulting from Example 11, were injected into two mice as described in Example 12. As with any foreign substance introduced into a mammal, the B cells, which form a part of the mouse's immune system, produced antibodies to each of the various proteins in the mixture. Each B cell can produce only a single type of specific antibody. Individual antibodies can specifically bind to the individual proteins.

B cells from the mouse spleen were fused with an established cell line of myeloma cells to produce a hybridoma. The hybridoma retained the characteristics of the fused B cells and are capable of producing antibodies.

The progeny of each independent B cell fused with a myeloma cell were grown separately. The antibodies (called monoclonal antibodies—MAbs) which each fused pair of cells produced and secreted into the culture media was individually tested to determine if the antibody recognized any one of the proteins in the partially purified salicylic acid binding protein mixture used to immunize the mice. The ELISA procedure, described in Example 13, was used for this test or screen. At that point, the inventors had a partially purified protein mixture and a series of hybridoma which produce antibodies specifically recognizing the proteins in that mixture.

The next step is called immunoprecipitation. In immunoprecipitation, antibodies produced by different hybridomas were separately incubated (mixed) with the partially purified protein mixture in order to determine which bound (recognized) the salicylic acid binding protein. The antibodies produced by each hybridoma were attached to sepharose beads using protein A. These beads were then systematically placed into samples of the partially purified protein mixture. When binding occurs between an antibody and a protein, the bound protein also becomes bound to the bead. The bead, including the bound protein, can then be separated from the mixture by centrifugation. The proteins which remained in the mixture because they were not bound by antibodies were then tested for salicylic acid binding activity. If binding activity remains, then the protein removed by reaction with a specific antibody is not the binding protein. If, on the other hand, the protein that reacts with the antibody is the salicylic acid binding protein, then its removal from the mixture also renders the remaining mixture incapable of binding salicylic acid.

As described in more detail in Example 14, all of the monoclonal antibodies which removed or precipitated a 280 kDa protein from the mixture also removed the salicylic acid binding activity. This clearly indicates that the protein, having an apparent molecular weight of 280 kDa as measured by SDS-PAGE, is the salicylic acid binding protein.

EXAMPLE 12

Monoclonal Antibody Production

The highly purified salicylic acid binding protein preparation obtained after the four chromatography steps of Example 11 was emulsified in an equal volume of Freund complete adjuvant. Aliquots containing about 50 mg of proteins were injected intramuscularly into each of two female Balb/c mice. The mice were injected two more times (two and five weeks later), each time with an additional 50 µg of proteins per mouse. The serum was then tested six weeks later by ELISA for binding to epitopes on the proteins present in the highly purified salicylic acid binding protein preparation as described in Example 13. A final intraperitoneal injection of 50 µg of protein per mouse was given and the fusion was performed three days later. The mice's spleen cells were fused with a P3X-derived mouse myeloma cell line according to the procedure of Galfre and Milstein (1981, Methods Enzymol. 73: 3–46). The culture media from –1400 independent fused cell lines (hybridoma) were screened by ELISA for activity to the highly purified salicylic acid binding protein preparation.

EXAMPLE 13

ELISA (enzyme linked immunosorotion assay)

All steps of ELISA test were performed at room temperature following the procedure described by Harlow and Lane (1988 Antibodies: A Laboratory Manual, Cold Spring Harbor Lab Press, Cold Spring Harbor, N.Y.). Approximately 2 µg of the highly purified salicylic acid binding protein preparation was added per microtiter plate well in 50 µl of coating buffer (50 mM carbonate, pH 9.6). After incubating the antigen solution in the well overnight, the solution was removed and the wells were washed three times with PBST buffer (100 mM phosphate, pH 7.5, 100 mM NaCl, 0.05% Tween 20). The remaining potential protein binding sites of the well were blocked by a 2 hour incubation with 200 µl of 2% bovine serum albumin (BSA) in PBST buffer. The blocking solution was then removed and the wells were washed three times with PBST buffer. Hybridoma culture media (50 µl) were added for a 2 hour incubation. The culture media were removed and the wells were washed four times with the BPST buffer. Fifty µl of a solution containing anti-mouse antibodies-alkaline phosphatase complexes (Sigma Chemical; diluted 1:1000 in the BPST buffer with 0.2% BSA) was added per well for a 2 hour incubation, followed by five washes with BPST buffer. Fifty µl of p-nitrophenyl phosphate (1 mg/ml in 10% dietheneamide, pH 9.6) was added to each well. After a suitable degree of color development (about 30 min), 50 µl of 4N NaOH was added to each well to terminate the reaction.

EXAMPLE 14

Immunprecipitation of Salicylic Acid Binding Protein

In standard assays, 100–500 µl of hybridoma culture media were incubated with 40 µl of protein A-sepharose beads (50% slurry) at 4° C. for 2 hours. The antibody-protein A-sepharose complexes were pelleted by centrifugation in a microfuge and were washed three times with RIPA buffer (150 mM NaCl, 5 mM EDTA, 1% sodium deoxycholate, 0.1% SDS, 10 mM Tris, pH 7.4) and one time with a citrate-NP-40 buffer containing 20 mM citrate pH 6.5, 5 mM $MgSO_4$ 10% glycerol, 150 mM KCl and 0.1% NP-40. The complexes were then incubated at 4° C. for 2 hours with 100 µl of partially purified salicylic acid binding protein obtained after three or four chromatography steps. These antigen-antibody-protein A-sepharose complexes were then pelleted. The supernatants were collected and assayed for the amount of salicylic acid binding activity remaining.

Figure 9A:
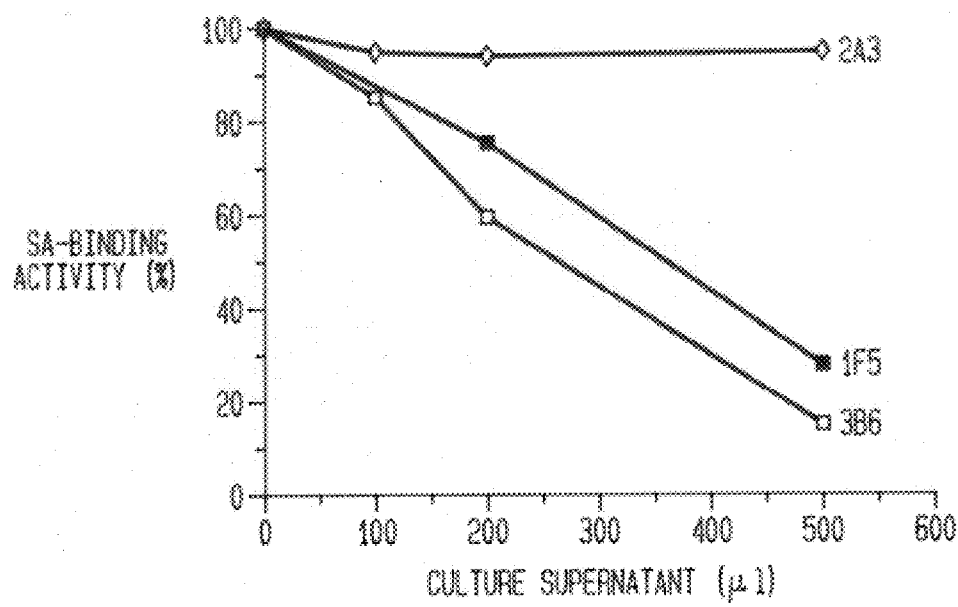
FIG. 9 illustrates the immunoprecipitation of salicylic acid binding activity and a 280 kDa protein by monoclonal antibodies.

As in FIG. 9A, increasing amounts of culture media (supernatants) from hybridomas (which contain monoclonal antibodies—MAbs) 3B6 and IF5 remove the salicylic acid binding activity from the mixture. In contrast, MAb 2A3 did not remove its binding activity.

Figure 9B:
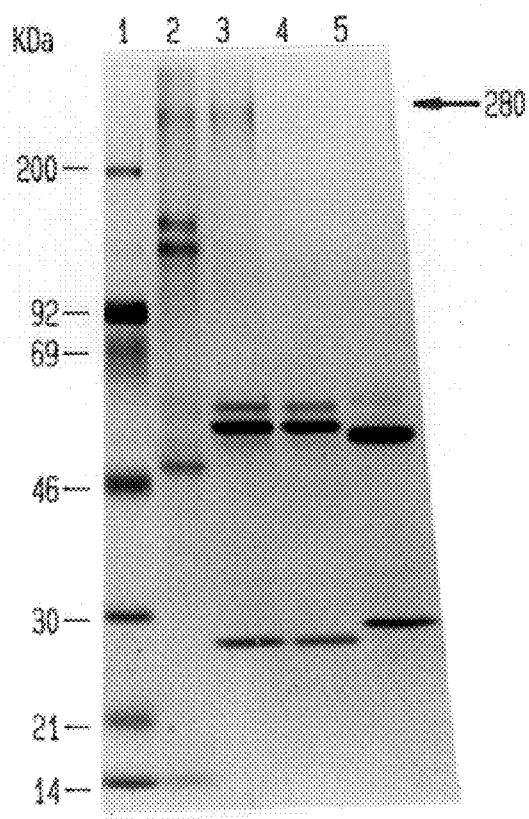

As shown in FIG. 9B, the beads removed from the antigen-antibody mixture by centrifugation were washed three times with 1×RIPA before being resuspended in protein sample buffer and subjected to SDS-PAGE (7.5–15%) analysis. Lane 1—size marker proteins; lane 2—antigen only (a blue dextran agarose fraction); lane 3—antigen plus MAb 3B6; lane 4—MAb 3B6 only; lane 5—antigen plus MAb 2A3. Analysis of the immune complex composition by SDS-PAGE indicated that the 280 kDa polypeptide was the only protein precipitated by MAbs 3B6 as illustrated in lane 3. In contrast, MAb 2A3 which did not remove the salicylic acid binding activity from the mixture also did not precipitate the 280 kDa protein, illustrated in lane 5.

It was found that those MAbs which immunoprecipitated the salicylic acid binding activity also immunoprecipitated the 280 kDa protein but not the other proteins present in the partially purified preparations. The other major protein in the purest preparation of salicylic acid binding protein was 150 kDa protein. It was not immunoprecipitated by the salicylic acid binding protein-specific MAbs. Moreover, MAbs that recognized and immunoprecipitated the 150 kDa protein (but not the 280 kDa protein), failed to immunoprecipitate the salicylic acid binding activity. These results strongly argue that the 150 kDa protein is not salicylic acid binding protein.

EXAMPLE 15

Immunoblot Analysis of Salicylic Acid Binding Protein

Four salicylic acid binding protein-specific MAbs (including 3B6 and IF5 described above) were used to detect the salicylic acid binding protein by immunoblot analysis. In this analysis, 50 μg of freshly prepared tobacco protein homogenates (labeled C in FIG. 10 for crude extract) made in the presence of β mercaptoethanol or 2 μg of tobacco salicylic acid binding protein partially purified (labeled P in FIG. 10) through the first three chromatography steps described in Example 11 were size fractionated by SDS-PAGE (7.5–15%). After size fractionation, the proteins were electrophoretically transferred to nitrocellulose filters in a solution of 48 mM Tris, 39 mM glycine pH 9.0, 20% methanol for 12–16 hrs. at 50 volts. The remaining protein binding sites on the nitrocellulose filters were blocked by incubation with a solution of 5% non-fat dried milk in Buffer B (100 mM phosphate pH 7.5, 100 mM NaCl, 0.1% Tween 20) for 1 hr at room temperature. The filters were then reacted with a 1:100 dilution, in Buffer B, of hybridoma culture media containing one of the four salicylic acid binding protein-specific MAbs (3B6, IF5, 2C11, and 7F10) or one of three MAbs which do not recognize the salicylic acid binding protein (5A8, 6E10, and PR-1). MAbs 5A8 and 6E10 were obtained from the same fusion from which the salicylic acid binding protein-specific MAbs were obtained. However, they failed to react with the partially purified salicylic acid binding protein mixture in the ELISA. MAb PR-1 specifically recognizes the 16 kDa pathogenesis-related proteins PR-1 of tobacco; these proteins are not made in uninfected plants such as those used for preparation of the homogenates. After incubation at room temperature, the filters were washed three times with Buffer B. The antigen-antibody complexes were detected using a 1:10,000 dilution of sheep anti-mouse antibodies conjugated to horseradish peroxidase using the ECL (Enhanced ChemiLuminescence) detection kit from Amersham.

Figure 10:
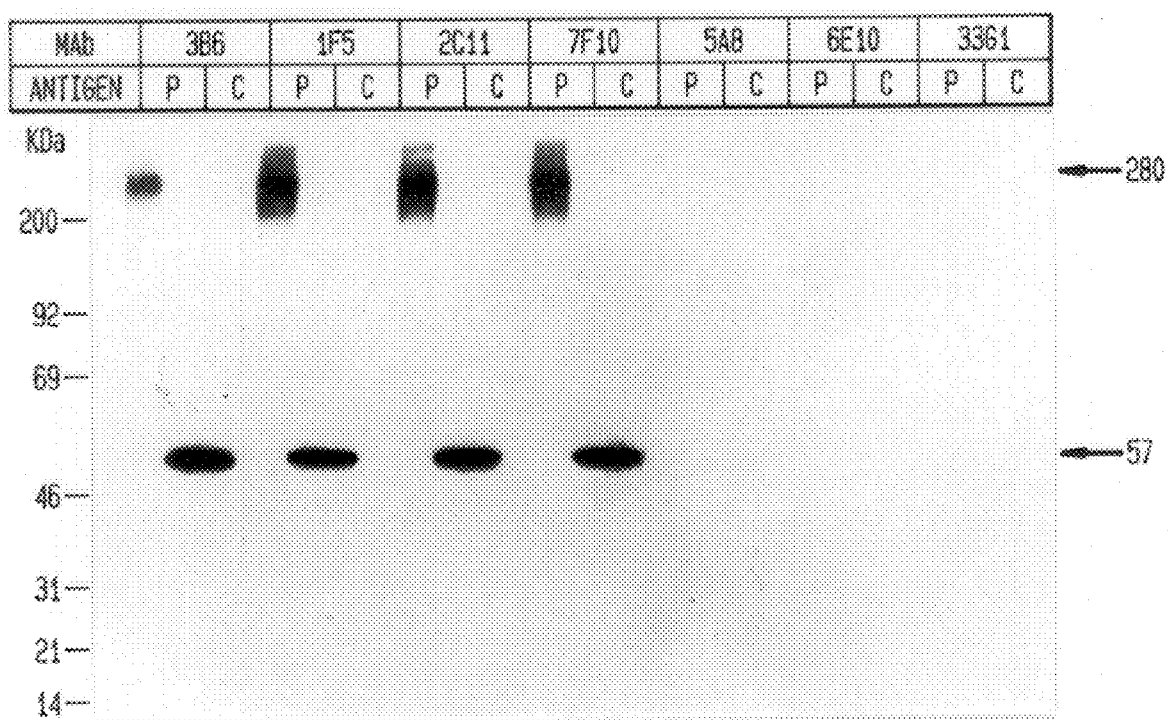
FIG. 10 illustrates an immunoblot analysis of salicylic acid binding protein.

The four salicylic acid binding protein-specific MAbs each recognized (bound to) the 280 kDa protein in the partially purified preparations of salicylic acid binding protein (FIG. 10). This is consistent with i) the copurification of the 280 kDa protein with the salicylic acid binding activity and ii) the immunoprecipitation of both the salicylic acid binding activity and the 280 kDa protein by each of these MAbs.

In contrast, the MAb's recognize only a 57 kDa protein, in freshly made tobacco leaf homogenates prepared as in Example 1 but with the addition of 15 mM β mercaptoethanol to the homogenization buffer. (FIG. 10). β mercapto-ethanol is a reducing agent which represses the activity of polyphenol oxidases that can cause crosslinking of proteins. These results indicate that one of the components of salicylic acid binding protein is the 57 kDa protein. Since the salicylic acid binding protein's native molecular weight, as determined by gel filtration, is approximately 240 kDa in the presence of 100 mm KCl, salicylic acid binding protein appears to be a multimeric complex. The complex may be composed of multiple subunits of only the 57 kDa protein or it may contain other proteins in addition to the 57 kDa protein. It appears that when the salicylic acid binding protein is prepared in the absence of reducing agents to decrease polyphenol oxidase activity, the subunits of the complex are crosslinked together. As a result these subunits are not dissociated under denaturing conditions such as during SDS-PAGE and thus migrate as a large protein (complex) of 280 kDa. The arrows indicate the position of the 280 kDa and 57 kDa proteins in FIG. 10.

Several, of the MAbs that bind to the tobacco 57 kDa protein and 280 kDa complex also recognize a 57 kDa protein in fresh homogenates from cucumbers. The salicylic acid binding activity from cucumber has similar affinity (Kd) and specificity as the tobacco salicylic acid binding protein. Like the tobacco salicylic acid binding protein, the cucumber salicylic acid binding protein also has a large native molecular weight (approximately 200 kDa). Thus, it appears that the cucumber salicylic acid binding protein is also a complex composed of multiple subunits at least one of which is probably the 57 kDa protein recognized by the MAbs made against the tobacco salicylic acid binding protein. It should be noted, however, that there may be some minor variation in molecular weight and Kd for salicylic acid binding protein from one plant species to the next. For example, cucumber derived salicylic acid binding protein appears to have an apparent average native molecular weight of about 200 kDa and a Kd of about 30±5 μM.

The model of salicylic acid binding protein is consistent with the inventors' initial observation that salicylic acid binding protein had an apparent native molecular weight of 650 kDa as determined by gel filtration chromatography of ammonium sulfate precipitated protein. Ammonium sulfate precipitation exacerbates the problem of aggregation and in the presence of polyphenol oxidases facilitates crosslinking. When this precipitation step was eliminated, salicylic acid binding protein had an apparent native molecular weight of 180–240 kDa. Note that after salicylic acid binding protein was fractionated on cellulose and initially chromatographed on sephacryl S-300 under low ionic conditions (20 mM citrate pH 6.5, 10 mM $MgSO_4$, 30 μg/ml PMSF), salicylic acid binding protein eluted with an apparent molecular weight of 180 kDa. In contrast, when gel filtration chromatography was done in the presence of modest ionic strength (100 mM KCl) salicylic acid binding protein's apparent native molecular weight was determined to be 240 kDa. Presumably at low ionic strength salicylic acid binding protein preferentially interacts with the matrix, causing its migration to be slightly retarded and thus its molecular weight to be underestimated.

In summary, several monoclonal antibodies raised against the highly purified salicylic acid binding protein immuno-precipitated the salicylic acid binding activity and a 280 kDa protein. This 280 kDa protein also copurified with the salicylic acid binding activity during the various chromatography steps, indicating that it was responsible for binding salicylic acid. The 280 kDa molecular weight of the denatured salicylic acid binding protein, as determined by SDS-PAGE, was similar to its apparent average native molecular weight of 240 kDa, as determined gel filtration in the presence of 100 mM KCl. The salicylic acid binding protein-specific MAbs also recognized the 280 kDa species after SDS-PAGE size fractionation and immunoblot analysis of partially purified salicylic acid binding protein. In contrast, in parallel size fractionation and immunoblot analysis of freshly prepared plant homogenates (made in the presence of reducing agents to decrease the activity of polyphenol oxidases), the four different salicylic acid binding protein-specific MAbs recognized (bound) only a 57 kDa protein. These results strongly suggest that the native salicylic acid binding protein is a heteromeric or homomeric complex containing the 57 kDa protein as a subunit. Upon extraction and subsequent purification of salicylic acid binding protein, the subunits of the complex appear to be covalently crosslinked, probably due to the action of polyphenol oxidases. The crosslinked complex remains active. However, the subunits cannot be dissociated even by SDS-PAGE and hence they migrate together as a large molecular weight entity of 280 kDa.

EXAMPLE 16

Isolation of a cDNA Clone which Encodes a Protein Recognized by MABs that Immunoprecipitate SA that Immunoprecipitate SA Binding Activity An aliquot of amplified λgt11 tobacco cDNA library (prepared from mature leaves of *N. tabacum* cultivar SR1)

was absorbed onto *E. coli* (Y1090) and plated at a density of 10,000 plaques per 150 mm plate containing LB-ampicillin. The bacteriophages were grown at 42° C. for 4 hours to induce lysis. Nitrocellulose filters precoated with 10 mM isopropyl thio-β-D-galactoside (IPTG) were overlaid on the plates and incubated for 2.5 hours at 37° C. to induce expression of the cDNA inserts. After the incubation, the filters were removed and blocked by incubating for 1 hour at 4° C. in BPST buffer (100 mM phosphate, pH 7.5, 100 mM NaCl, 0.1% Tween 20) containing 5% nonfat milk, and washed three times with BPST buffer for a few minutes each. Blots were probed with diluted hybridoma media (1:100) in BPST buffer containing 0.2% BSA for 1 hour, and briefly washed as above three times with PBST buffer. The antigen-antibody complexes were detected with a 1:10,000 dilution of sheep antimouse IgG antibodies conjugated to horseradish peroxidase using the ECL (Enhanced Chemiluminescence) detection kit from Amersham. An immunopositive bacteriophage clone (λCK1) was identified and purified by sequential low-density plating and immunoblotting by following the same procedure described above. Bacteriophages of the purified clone were amplified and DNA was purified by following the standard procedure described in Molecular Cloning: A Laboratory Manual, 2nd Edition, Editors J. Sambrook, E. F. Fritsch, and T. Maniatis 1989, Cold Spring Harbor Laboratory Press. The purified bacteriophage DNA was digested with restriction enzyme EcoR I and the cDNA insert (approximately 1.9 kb) was purified and subcloned into the EcoRI site of the plasmid Bluescript SK II$^+$ generating the plasmid designed pCK1. pCK1 has been deposited with the ATCC under the Budapest Treaty.

EXAMPLE 17

DNA Sequence Determination of the cDNA Insert of pCK1

DNA sequencing was performed by the dideoxynucleotide chain-termination method (Sanger et al., Proc. Natl. Acad. Sci. USA 1977, 74: 5463), using the Sequenase kit from United States Biochemicals and (α-$^{35}$S)dATP. The complete sequence of the cDNA insert has been determined for one strand and partially determined for the second strand. Table 5 shows the DNA sequence and predicted amino acid sequence are shown. Sequences corresponding to the amino acid sequences from the tryptic peptides are underlined.

TABLE 5

DNA and predicted amino acid sequence of pCK1

```
              10                    30                      50
ctctaagtttcgaccatcaagcgcatatgattcccctttcttgacaacaaatgctggtgg
  S  K  F  R  P  S  S  A  Y  D  S  P  F  L  T  T  N  A  G  G 70                    90                     110
tcctgtctacaacaacgtttcttccttgactgttggacctagagggcctgttcttcttga
  P  V  Y  N  N  V  S  S  L  T  V  G  P  R  G  P  V  L  L  E 130                   150                     170
ggattatcacttaatagagaagctcgcgactttgatcgtgagcggatacctgagcgtgt
  D  Y  H  L  I  E  K  L  A  T  F  D  R  E  R  I  P  E  R  V 190                   210                     230
tgttcatgctagaggtgccagtgcaaaaggtttctttgaagtcactcatgatatttctca
  V  H  A  R  G  A  S  A  K  G  F  F  E  V  T  H  D  I  S  H 250                   270                     290
tcttacctgtgctgatttctccgagcgcctggggttcaaacacctgttatttgccgttt
  L  T  C  A  D  F  L  R  A  P  G  V  Q  T  P  V  I  C  R  F 310                   330                     350
ctctactgtcgtccatgagcgtggaagccccgagtcccttagggacattcgtggttttgc
  S  T  V  V  H  E  R  G  S  P  E  S  L  R  D  I  R  G  F  A 370                   390                     410
tgtcaaattttacaccagagagggtaactttgatctggttggaaacaacgtccccgtctt
  V  K  F  Y  T  R  E  G  N  F  D  L  V  G  N  N  V  P  V  F 430                   450                     470
ctttaatcgtgatgcaaaatcgttccctgacacgattcgtgcactgaaaccaaatccaaa
  F  N  R  D  A  K  S  F  P  D  T  I  R  A  L  K  P  N  P  K 490                   510                     530
gtcacacattcaggaatactggaggatccttgatttcttctctttccttccggagagttt
  S  H  I  Q  E  Y  W  R  I  L  D  F  F  S  F  L  P  E  S  L 550                   570                     590
gcatacttttgcctggttttcgatgatgtttgtctcccgacagattacagacacatgga
  H  T  F  A  W  F  F  D  D  V  C  L  P  T  D  Y  R  H  M  E 610                   630                     650
aggttatggtgttcacgcctatcaattaatcaacaaggctgggaaagcacattatgtgaa
  G  Y  G  V  H  A  Y  Q  L  I  N  K  A  G  K  A  H  Y  V  K 670                   690                     710
gtttcactggaaaccaacttgtggtgtcaagtgcatgtcggaggaagaagctattagggt
  F  H  W  K  P  T  C  G  V  K  C  H  S  E  E  E  A  I  R  V
```

TABLE 5-continued

DNA and predicted amino acid sequence of pCK1

```
            730              750              770
cggaggtacaaatcatagccacgccaccaaggatctctacgattcgattgctgctggaaa
 G  G  T  N  H  S  H  A  T  K  D  L  Y  D  S  I  A  A  G  N 790              810              830
ctatcccgagtggaaacttttttatccaaattatggacactgaggatgtagacaaattcga
 Y  P  E  W  K  L  F  I  Q  I  M  D  T  E  D  V  D  K  F  D 850              870              890
ctttgatcctcttgatgtaaccaagacctggcctgaggatatcttgccattgatgccagt
 F  D  P  L  D  V  T  K  T  W  P  E  D  I  L  P  L  M  P  V 910              930              950
tggacgattggtacttaacaggaatatcgataacttctttgctgagaacgagcagctcgc
 G  R  L  V  L  N  R  N  I  D  N  F  F  A  E  N  E  Q  L  A gtttaaccctggccatattgtccctggtctttactattcggaggacaagcttctccagac
 F  N  P  G  H  I  V  P  G  L  Y  Y  S  E  D  K  L  L  Q  T 1030             1050             1070
taggatattcgcgtatgctgatactcagagacaccgtattggaccaaactatatgcagct
 R  I  F  A  Y  A  D  T  Q  R  H  R  I  G  P  N  Y  M  Q  L 1090             1110             1130
tcctgttaatgctcccaagtgtgctcatcacaataatcaccgcgatggtgccatgaactt
 P  V  N  A  P  K  C  A  H  H  N  N  H  R  D  G  A  M  N  F 1150             1170             1190
catgcatcgcgatgaagaggtggattatttgccctcaaggttcgatccttgtcgtcatgc
 M  H  R  D  E  E  V  D  Y  L  P  S  R  F  D  P  C  R  H  A 1210             1230             1250
tgaacagtacccaattccttctcgtgtcttgacaggaaggcgtgaaatgtgtgtcattga
 E  Q  Y  P  I  P  S  R  V  L  T  G  R  R  E  M  C  V  I  E 1270             1290             1310
gaaagagaacaacttcaagcaggcaggagaaagatacagatcctgggaacctgacaggca
 K  E  N  N  F  K  Q  A  G  E  R  Y  R  S  W  E  P  D  R  Q 1330             1350             1370
agacagatatgttagcaaatgggttgagcatttatccgatccacgagtcacttatgagat
 D  R  Y  V  S  K  W  V  E  H  L  S  D  P  R  V  T  Y  E  I 1390             1410             1430
acgcagtatatggatatgctccctgtctcaggctgacaagtcttgtggtcagaaggtcgc
 R  S  I  W  I  C  S  L  S  Q  A  D  K  S  C  G  Q  K  V  A 1450             1470             1490
ttctcgtctcactttaaagcctacaatgtgatgaagactaagatgaaaacactactggga
 S  R  L  T  L  K  P  T  M  *

1510             1530             1550
aaacgtctcaagttgcagtttgaaggagtactaaaccaagaaaagcattacgtttgtgtg 1570             1590             1610
tttttgctataaagtgtactgtttcgttttatgttctgtttgtaccaaactttgatatct 1630             1650             1670
tgtgtttactatgacacaatatatgttgcacttgaataaggtacagatgtatgttcaagt 1690             1710             1730
actgtggtcatcttctttctattttaccttgtttcacactttttaagcttttgtgccaaa 1750             1770             1790
attatgtcatacttgctcattttggtgcttgaagtatacccctcaattctataatgccact 1810             1830             1850
ggtattgtagttttattgacatgttaataagaaagctgctactctgtcttccgttcaa
```

EXAMPLE 18

Isolation of a Full Length cDNA for SABP

The cDNA pCK1 does not include the aminoterminal methionine and is therefore not a full-length clone. From the predicted molecular weight of the polypeptide product (57 kDa) it is assumed that pCK1 is near full-length. In order to isolate a full-length cDNA copy, a library of tobacco cDNA is plated and screened with radio-labeled pCK1 cDNA using techniques well known in the art. Clones identified are sequenced and the 5' untranslated region and initiating methionine of the cDNA are identified.

EXAMPLE 19

Amino Acid Sequence of Several Tryptic Peptides of the SABP

Immunoprecipitation with one of the SABP-specific MAbs (MAb 3B6; see Example 14) was used as the final purification step to purify SABP from about 300 mg of highly purified SABP fraction obtained after the four steps of chromatography described in Example 11. The immunoprecipitated SABP complexed with MAbs was then subject to SDS-PAGE (5–15%) (See Example 7) and SABP band was identified by Coomassie Blue staining. The band of SABP was excised and submitted for peptide sequencing to W. M. Keck Foundation Biotechnology Laboratory of Yale University. Amino acids composition of an aliquot (10%) of the submitted gel was first analyzed to verify that there was sufficient protein to proceed. Tryptic digestion was then performed in the gel matrix followed by elution and separation of the resulting peptides by high performance liquid chromatography (HPLC). Several peaks from the HPLC profile potentially suitable for sequencing were further subject to laser desorption mass spectrophotometer (LDMS) to ensure that each of these peaks indeed contain a peptide and contained predominantly one peptide. Gas-phase sequence analysis was then performed on these peptides. Below is their amino acid sequences (top line) and the corresponding predicted amino acid sequence from the cDNA insert of pCK1 (bottom line).

```
U572-1  E G N F D L V G N N F P V F F
        I R
cDNA    - - - - - - - - - - V - - - -
        N -

N994-1  S F T P D R Q E R
cDNA    - W E - - - - D -

D839    W V E A L S D P R
cDNA    - -   - H - -   - -   -
```

The occasional mismatch of protein-derived sequence and cDNA predicted sequence may be due to the different tobacco cultivars used as starting material for the protein purification and cDNA cloning experiments. Alternatively, the discrepancy in several amino acid residues may have resulted from the existence of different SABPS isozymes in tobacco.

EXAMPLE 20

Cloning the SABP cDNA Using PCR Techniques and Degenerate Oligonucleotides Designed to Known Peptide Sequence The peptide sequences described in example 18 can be used to design degenerate oligonucleotides which can be used as primers in a PCR reaction for the cloning of the SABP cDNA. In addition to degenerate nucleotide sequence, primers include at their 5' end a restriction endonuclease recognition site and a GGGC clamp or extension for efficient cleavage of the restriction site. Primers are designed in sense and antisense to the known peptide sequence and sense and antisense primers are designed with different restriction site extensions to enable easy cloning into an appropriate vector. Typical primers are based on the sequence of between 6 and 10 amino acid residues. For the amino acid sequence U572-1 described in example 18 the following primers would be suitable:

```
5'-GA(A/G)GG(N)AA(C/T)TT(C/T)GA(C/T)(C/T)T(N)GT
and:
5'-C(G/T)(A/T/G)AT(G/A)AA(G/A)AA(N)AC(N)GG
```

N is an abbreviation of all four nucleotides which can alternatively be replaced by inosine. In each case, and as described above, a different restriction enzyme recognition site and GGGC clamp is added at the 5' end to expedite subsequent cloning of the PCR-generated fragment.

For peptide fragments N994-1 and D839 similar sense and antisense oligonucleotides can be designed, and these can be used in combination with primers designed to other peptide sequences in order to generate PCR fragments of sufficient size for cloning.

Suitable substrates for PCR reactions using the degenerate oligonucleotides described above are reversed transcribed RNA from tobacco and cDNA libraries of tobacco. Alternatively genomic libraries of tobacco or genomic DNA may be used. PCR products thus generated are fractionated in acrylamide or agarose gels, cleaved with the appropriate restriction endonucleases and cloned into suitable DNA cloning vectors. Clones found to carry inserts which match the known amino acid sequence are used as probes to screen cDNA and genomic libraries. The techniques described above for PCR and cloning are well known in the art (see "Current Protocols in Molecular Biology", Wiley and Sons, New York, (1991)).

EXAMPLE 21

Overexpression of BABP in Transcenic Plants

The cDNA described in example 18 is expressed at high levels in transgenic plants. The cDNA is cloned into a plant expression casette behind a promoter expressed at high levels in transgenic plants and upstream of a cleavage and polyadenylation signal which is known to function in plants. A preferred promoter is the CaMV 35S promoter and a preferred cleavage and polyadenylation signal is the nopaline synthase cleavage and polyadenylation signal. The expression cassette is transferred to binary vector (pCGN154;—Alexander et al., PNAS 90: 7327-(1993) for Agrobacterium transformation and a direct gene transfer vector (pCIB3064; Koziel et al., Biotechnology 11: 194–200) for direct gene transfer. Agrobacterium is particularly suitable for the transformation of dicotyledonous species and direct gene transfer is particularly suitable for the transformation of monocotyledonous species. These techniques are well known in the art and are described in the two above-mentioned publications. transgenic plants are screened for high-level expression of the SABP transgene by Western analysis using antibodies which recognize SABP.

Alternatively, promoters for the expression of SABP can be selected which have tissue specific expression pattern and would thus localize the increase in SABP to particular cell types.

EXAMPLE 22

SABP has Homology to Catalase and Catalase Activity

The amino acid sequence deduced from the cDNA sequence of the cloned SABP gene revealed high homology (60–90%) to catalases of other organisms, with highest similarity to plant catalases. To determine whether or not the SABP had catalase activity, its hydrogen peroxidase degrading activity was measured directly. Highly purified SABP obtained after four chromatography steps (Chen et al., *Proc. Natl. Acad. Sci. USA*, 90: 9533 (1993)) exhibited high specific catalase activity (3000–10,000 U/mg) and this activity could be specifically immunoprecipitated by SABP-specific hAbs. The sizes of the SABP complex (240–280 kDa) and its subunits (57 kDa) are consistent with the structure of known catalases which are composed of four identical or similar subunits of 50–60 kDa.

EXAMPLE 23

Inhibition of SABP-Associated Catalase Activity with SA

In the presence of SA, the catalase activity of the highly purified SABP was inhibited by 80% (Table 6). A similar level of inhibition of catalase activity by SA (~70%) was also observed with crude extracts; inhibition appeared to be reversible since the catalase activity could be largely recovered by extensive dialysis. To assess the functional relevance of catalase inhibition by SA, several SA analogues, with or without biological activity in inducing plant PR genes and disease resistance, were compared for their ability to inhibit the catalase activity of SABP (Table 6).

Catalase activity of SABP was assayed over 3 minutes at room temperature in a 1 ml-mixture containing 20 mM citrate, pH 6.5, 5 mM $MgSO_4$, 1 mM $H_2O_2$, 1 mM SA or its analogues and 500 ng of SABP purified from four chromatography steps (Chen et al., *Proc. Natl. Acad. Sci. USA*, 90: 9533 (1993)). Aliquots (50 $\mu$l) were removed from the assay mixture at 30 second intervals to assay for amount of $H_2O_2$ remaining using the luminol method as has been described by Warm and Laties, *Phytochem.* 21: 827 (1982) except for the following modifications: 50 $\mu$l of test solution and 50 $\mu$l of luminol (0.5 mM in 0.2N $NH_4OH$, pH 9.5) were added to 0.8 ml of 0.2N $NH_4OH$, pH 9.5 in a test tube. The tube was placed in the measuring chamber and assay was initiated with automatic injection into the mixture of 100 $\mu$l of 0.5 mM $K_3Fe(CN)_6$ in 0.2N $NH_4OH$, pH 9.5. Measurements were integrated over 5 second periods. $H_2O_2$ was calculated from the standard curve constructed with known amounts of $H_2O_2$. Rate constants of SABP catalase activity in the presence or absence of SA or its analogues were then calculated based on a first-order mechanism.

2,6-dihydroxybenzoic acid and acetylsalicylic acid, both of which are active inducers of PR genes and resistance, were effective inhibitors of the catalase activity of SABP. Quantitatively 2,6-dihydroxybenzoic acid was somewhat stronger and acetylsalicylic acid was weaker than SA for inhibition of catalase. 2,3-dihydroxybenzoic acid, which has only weak biological activity, was a poor inhibitor while five structurally similar but biologically inactive analogues were ineffective in inhibiting the catalase activity. Moreover, the analogues' effectiveness in inhibiting SABP's catalase activity correlated with their ability to compete with [$^{14}$C] SA for binding to SABP, indicating that binding of SA and its analogues to SABP was responsible for the inhibition of the catalase activity.

TABLE 6

Inhibition of catalase activity and [$^{14}$C]SA binding of SABP by SA and its analogues.

| | Inhibition (%) | | |
| --- | --- | --- | --- |
| SA and analogues | Biological Activity* | Catalase Activity | [$^{14}$C]SA binding** |
| 2-Hydroxybensoic acid (SA) | + | 80.5 | 89 |
| 2,6-Dihydroxybenzoic acid | + | 91.3 | 92 |
| Acetylsalicylic acid | + | 53.6 | 48 |
| 2,3-Dihydroxybenzoic acid | ± | 15.3 | 9 |
| 3-Hydroxybenzoic acid | − | 3.1 | 1 |
| 4-Hydroxybenzoic acid | − | 4.1 | −2 |
| 2,4-Dihydroxybenzoic acid | − | 5.2 | −4 |
| 2,5-Dihydroxybenzoic acid | − | 3.2 | 1 |
| 3,4-Dihydroxybenzoic acid | − | 5.1 | 0 |

*Based on ability to induce resistance or PR gene expression or to inhibit wounding/elicitor-induced synthesis of protease inhibitors (White, Virology 99:410 (1979); van Loon, Neth. J. Plant Path. 89:265 (1983); Abad et al., Antiviral Ass. 9:315 (1988); Doherty et al., Physiol. Mol. Plant Pathol. 33:377 (1988)).
**Previously published data (Chen et al., Proc. Natl. Acad. Sci. USA. 90:9533 (1993)).

EXAMPLE 24

Catalase Inhibition In Vivo

Figure 11:
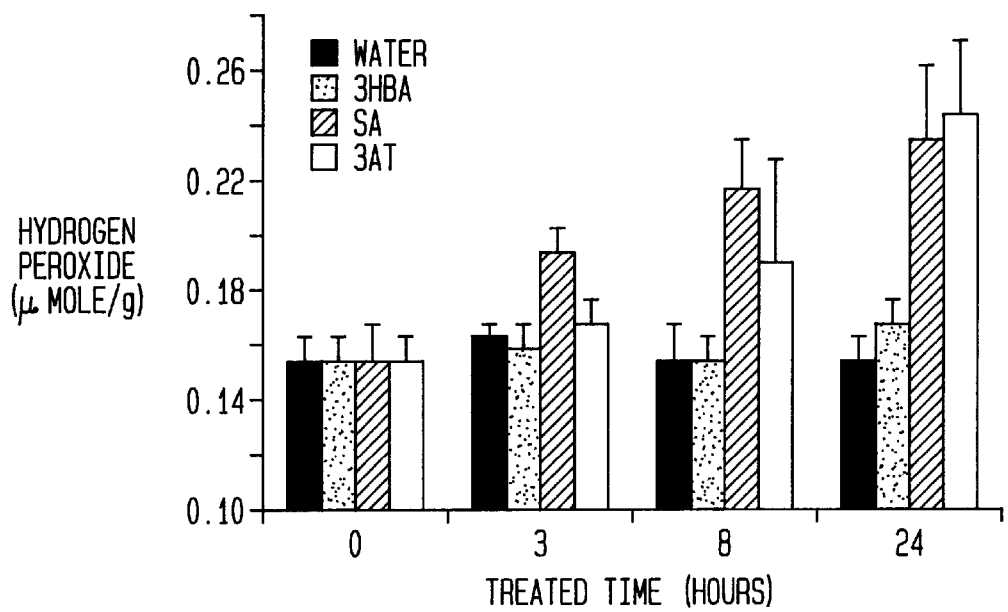
FIG. 11 illustrates the increase in abundance of $H_2O_2$ in SA or 3AT treated tobacco leaves.

The abundance of $H_2O_2$ was monitored in leaves following treatments with SA, 3-hydroxybenzoic acid (a biologically inactive analogue of SA), and 3-amino-1,2,4-triazole (3AT; a specific inhibitor of plant and animal catalases). The abundance of $H_2O_2$ increased in SA- or 3AT-treated tobacco leaves by 50–60% over the control levels observed in water-treated leaves. (FIG. 11) By contrast, 3-hydroxybenzoic acid was unable to enhance the in vivo abundance of $H_2O_2$ consistent with its ineffectiveness in both binding SABP and inhibiting catalase activity. Thus, elevated levels of $H_2O_2$, and in turn, enhanced oxidative stress in vivo, were consistent with inhibition of catalase activity by SA observed in vitro.

Figure 12:
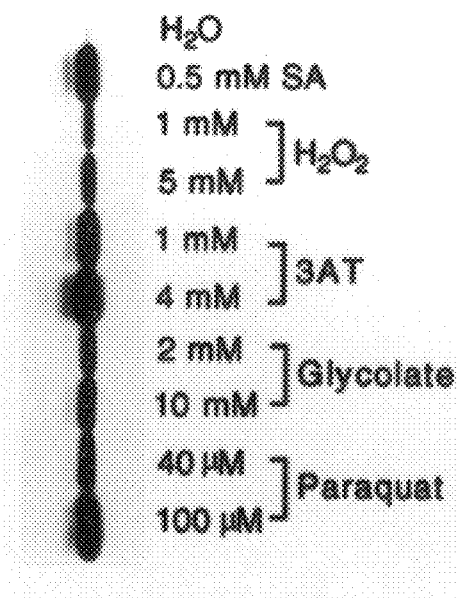
FIG. 12 illustrates the induction of protein synthesis.

PR gene expression is both induced by SA and associated with the development of SAR. Therefore, it was of interest to test whether SA's mechanism of action for the induction of PR genes was via its inhibition of catalases which leads to enhanced $H_2O_2$ levels. To address this question, $H_2O_2$ abundance was artificially raised in tobacco leaves by treating with $H_2O_2$ or compounds which either inhibit the catalase activity, like SA itself, or promote generation of $H_2O_2$ in vivo. Injection of $H_2O_2$ or the catalase inhibitor 3AT into tobacco leaves induced the expression of PR-1 genes. (FIG. 12) PR-1 gene expression was also induced by treating tobacco leaves with glycolate (an intermediate in photorespiration which serves as a substrate for the generation of $H_2O_2$ by glycolate oxidase present in leaves) and with paraquat (a herbicide which can be reduced in vivo and subsequently reoxidized by transfer of its electrons to oxygen to form superoxide anion; superoxide can be converted either spontaneously or enzymatically by superoxide dismutase to $H_2O_2$). Thus, the SA signal appears to be propagated through $H_2O_2$ which may act as a secondary messenger, to activate defense-related PR genes.

EXAMPLE 25

Expression of Antisense RNA to the SABP Gene in Transgenic Plants

Antisense RNA to the SABP gene is expressed in transgenic plants by the cloning of the cDNA described in example 18 behind a suitable promoter in antisense orientation. The cDNA is cloned into a plant expression casette behind a promoter expressed at high levels in transgenic plants and upstream of a cleavage and polyadenylation signal which is known to function in plants. A preferred promoter is the CaMV 35S promoter and a preferred cleavage and polyadenylation signal is the nopaline synthase cleavage and polyadenylation signal. The expression cassette is transferred to a binary vector (pCGN1540— Alexander et al., *PNAS* 90: 7327 (1993)) for Agrobacterium transformation and a direct gene transfer vector (pCIB3064; Koziel et al., Biotechnology 11: 194–200) for direct gene transfer. Agrobacterium is particularly suitable for the transformation of dicotyledonous species and direct gene transfer is particularly suitable for the transformation of monocotyledonous species. These techniques are well known in the art and are described in the two above-mentioned publications. Transgenic plants are screened for expression of SABP antisense RNA by Northern analysis and plants which express at high levels are found to have enhanced resistance to plant pathogens.

Alternatively, promoters for the expression of SABP can be selected which have tissue specific expression pattern and would thus localize the effects of antisense expression to particular cell types.

EXAMPLE 26

Expression of a Salicylic Acid Insensitive Catalase Gene in Transgenic Plants The inventors also have conducted tests which indicate that catalases from non-plant sources such as fungi and animals are insensitive to inhibition by salicylic acid. Genes or cDNA copies for several of these catalases have been cloned (e.g. Scandalios, J. G. et al., *Proc. Natl. Acad. Sci. USA*, 77 (1980) 5360–5364; Bell, G. I. et al., *Nucleic Acids Res.*, 14, (1986), 5561–5562; Hartig, A. et al., *Eur. J. Biochem*, 160, (1986) 487–490). A gene encoding one of these catalases can be introduced and expressed in a plant in the sense orientation using appropriate regulatory sequences (e.g. CaMV 35S promoter and nopaline synthase cleavage and polyadenylation signal) and vectors (e.g. PCGN 1540 or pCIB3064) as described in Example 25.

Catalase is a tetrameric complex of four subunits. Subunits encoded by different members of the catalase gene family in a given plant species form active heteromeric complexes which contain subunits encoded by two or more genes (Ni et al., Biochem J. 269: 233, 1990). A heteromeric complex between the endogenous plant catalase subunits and the introduced non-plant catalase subunit may not be able to form, because the subunits are too divergent. In this case the resulting homomeric catalase encoded by the introduced animal gene will not be inhibited by salicylic acid and hence the plant should become more sensitive to pathogens. Alternatively, the plant and non-plant encoded catalase subunits may together form a complex which is catalytically inactive. This would result in transgenic plants which are more resistant to pathogens. Also a heteromeric enzymatically active complex might be formed. This complex might be insensitive or sensitive to salicylic acid. If it is sensitive to SA, its phenotypes would be the same as the untransformed parental plant. However, if the heteromeric complex is insensitive, the transgenic plant should become more sensitive to pathogen attack.

EXAMPLE 27

Inhibition of Catalase by Expression of Antisense RNA to the SABP/Gene in Transgenic Tobacco Plants Activates PR-1 Gene Expression and Enhances Resistance to Tobacco Mosaic Virus (TMV).

Transgenic tobacco plants were constructed that constitutively express, under control of the CaMV 35S promoter, a cDNA copy of (from clone pCK1, Chen et al., Science 262: 1883, 1993) one member of the tobacco SABP/catalase gene family. The cDNA was inserted, relative to the promoter, in an antisense orientation such that the RNA produced was complementary to the mRNA synthesized from the endogenous tobacco catalase genes. The cDNA was inserted into the XbaI and SstI sites of pRT100 (Töpfer et al., Nucl. Acids Res. 15: 5890, 1987) between the 35S promoter and polyadenylation signal of CaMV strain Cabb B-D. The resulting plasmid was designated pCK4. The fragment containing the 35S promoter, SABP/catalase cDNA, and polyadenylation signal sequences was excised from pCK4 with SphI, blunt-ended with Klenow fragment, and cloned into the KpnI site of the Agrobacterium-based binary vector pGA482. Using the leaf disk transformation procedure (Horsch et al., Science 227: 1229, 1984), transgenic *Nicotiana tabacum* (*N.t.*) cultivar Xanthi nc were constructed.

Figure 14:
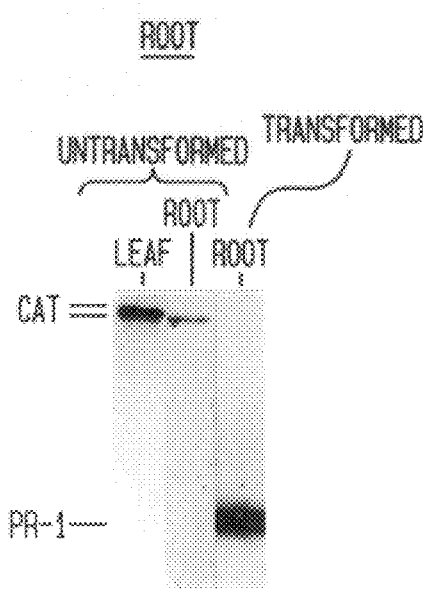
FIG. 14 illustrates an immunoblot analysis of PR1 expression based upon catalase activity from root tissue.
Figure 13A:
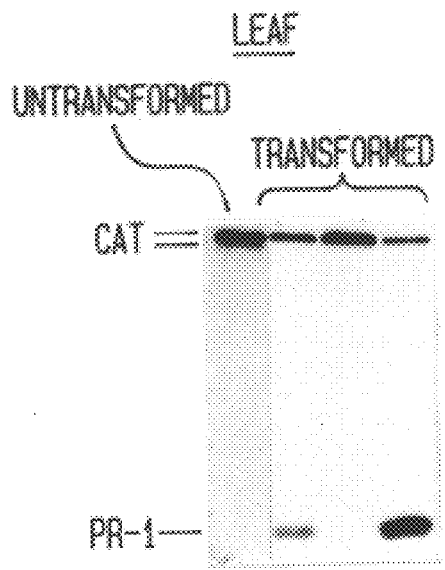
FIG. 13A illustrates an immunoblot analysis of PR1 expression based upon catalase activity from leaf tissue.

Tissues from these antisense transgenic plants and from untransformed control tobacco plants were analyzed to determine the levels of catalase protein and PR-1 protein using immunoblot analysis with a combination of anti-SABP/catalase monoclonal antibodies (3B6) and anti-PR-1 monoclonal antibody (33G1; FIG. 13A and B and FIG. 14). Leaves of untransformed plants did not express PR-1 genes in the absence of treatment by inducing chemicals such as SA or infection with TMV. The leaves of untransformed plants contained both a major, higher molecular (HMW) form and minor, low molecular weight (LMW) form of the catalase subunits. In leaves of antisense transgenic plant synthesis of the LMW form was essentially eliminated, while synthesis of the major HMW form was inhibited to varying extents in the different transgenic lines. The inventors found that the greater the level of inhibition of the catalase synthesis in the different transgenic lines, the higher the production of PR-1 proteins (FIG. 13A). For example, in the transgenic line where the catalase protein level was only modestly reduced (the third lane under Leaf in FIG. 13A), there was little, if any, production of PR-1 protein. By contrast, in the transgenic line where the catalase protein level was very substantially diminished (the fourth lane under Leaf in FIG. 13A), a high level of PR-1 protein accumulated.

Figure 13B:
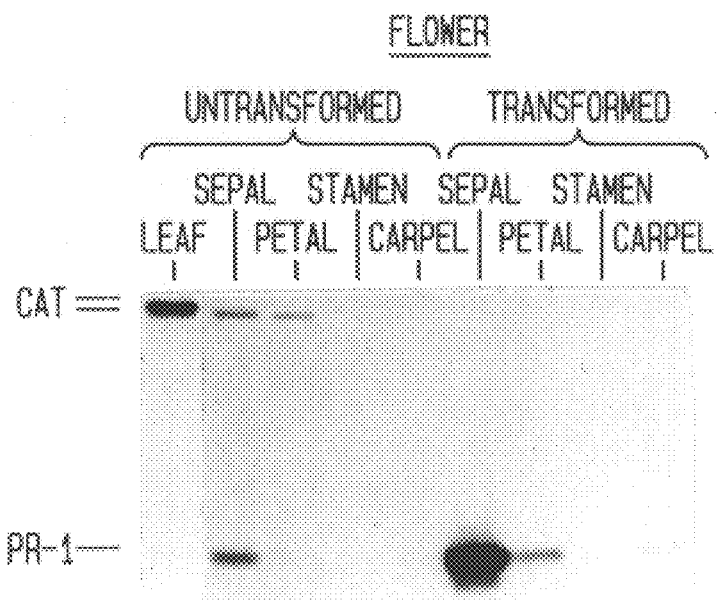
FIG. 13B illustrates an immunoblot analysis of PR1 expression based upon catalase activity from flower tissue.

In the sepals and petals of flowers (FIG. 13B) and in roots (FIG. 14) only the LMW form of catalase subunit is produced in untransformed plants. Its synthesis is effectively inhibited in these organs of the antisense transgenic plants and PR-1 gene expression was found to be constitutive.

Figure 15:
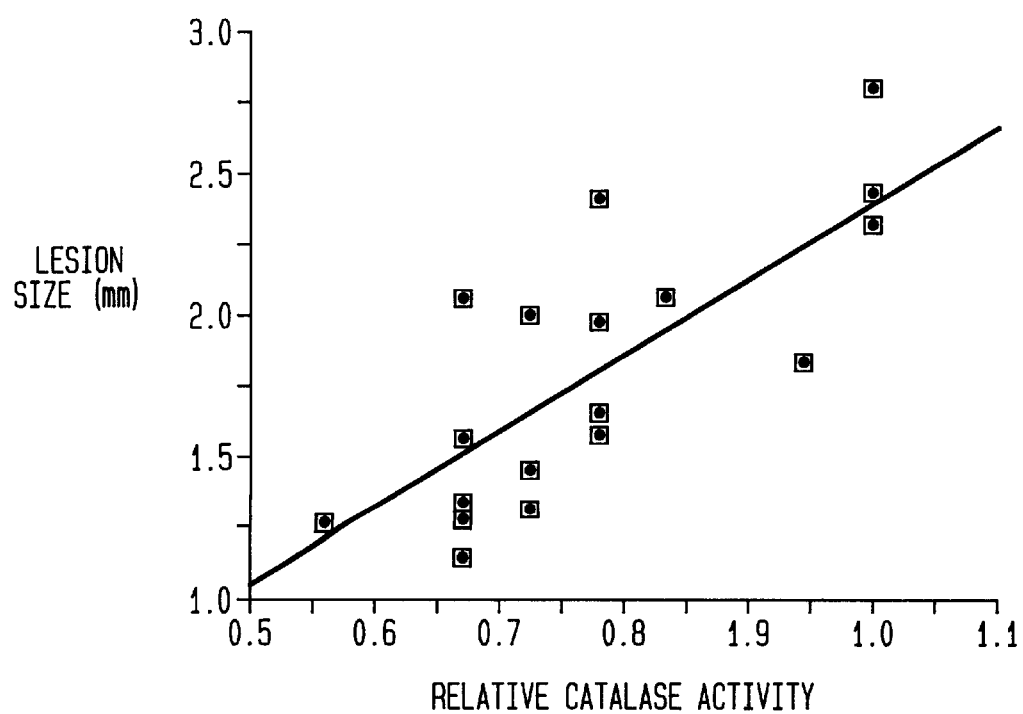
FIG. 15 is a graph of relative catalase enzyme activity levels of both transgenic and untransformed lines verses the size of TMV-induced lesions.

Reducing catalase protein levels, and hence catalase enzyme activity in the antisense transgenic plants also enhanced resistance to TMV infection. When the relative catalase enzyme activity levels in the leaves of 18 different antisense transgenic lines and the untransformed parental line was grafted versus the size of TMV-induced lesions formed on the various lines at 6 days after inoculation, it was found that there is a good correlation between reduced catalase activity and enhanced resistance as measured by a reduction in lesion size (FIG. 15), The results suggest that blocking catalase action leads to induction of defense responses such as PR-1 protein synthesis and enhanced disease resistance.

EXAMPLE 28

Most Abiotic Inducers of PR Gene Expression and Acquired Resistance Act Through SA.

To assess the role of SA in chemically induced PR-1 gene expression, leaves of N.t. cultivar Xanth inc plants were injected with polyacrylic acid (0.1 mM), thiamine-HCl (1 mM), α-amino butyric acid (50 mM), barium chloride (BaCl, 20 mM), 2,6-dichloro-isonicotinic acid (INA, 1 mM) or water and levels of total SA (free SA and its glucoside) were monitored (Table 7). The SA/SAG valves are given in micrograms per gram fresh weight of leaf tissue and represent averages of values from 3–6 treated plants at 6 days past injection. The concentrations of chemicals used strongly induced PR-1 protein accumulation, as determined by immunoblot analysis with a PR-1 specific monoclonal antibody (33G1), and also induced enhanced resistance to TMV, as determined by reduction in lesion size. For determination of reduction in lesion size, longitudinal halves of 2 leaves on 3–6 plants were injection with chemicals, and six days later the entire leaf was infected with TMV. Twenty lesions were measured on each half of the leaf seven days post infection; the values given represent the average percent reduction in lesion diameter in the treated leaf half compared to the untreated half. Similar results were obtained by comparing lesion size to that of control, water-injected plants (data not shown). Treatment with all of the above chemicals, except INA, resulted in elevated levels of total SA. Neither injection of water or wounding induced PR-1 gene expression, enhanced resistance, or elevated SA levels. This result argues that many abiotic inducers of PR gene expression and acquired resistance act by elevating SA levels.

EXAMPLE 29

2.6 Dichloro-Isonicotinic Acid, like SA, Acts by Binding Catalase and Inhibiting its Enzymatic Activity INA treatment induces resistance to a variety of pathogens (Métraux et al., In Advanced in Molecular Genetics of Plant-Microbe Interactions 1: 432, 1991, Kluwer Academic Publishers, Dordrecht; Ward et al., Plant Cell 3: 1085, 1991; Uknes et al., Plant Cell 4: 645, 1992). It also activates a common set of genes whose expression is induced systemically after local infection of tobacco by TMV. This group of genes is also turned on by SA treatment (Ward et al., Plant Cell 3: 1085, 1991). INA, however, does not act through SA, as shown in Example 28, Table 7.

In 1984, Kirkman and Gaetani (Proc. Natl. Acad., Sci. U.S.A. 81 :4343) demonstrated that bovine catalase tightly binds nicotinamide adenine dinucleotide phosphate (NADPH) and nicotinamide adenine dinucleotide (NADH). However, binding of NADPH or NADH (NAD(P)H) was shown not to be required for or effect catalase's enzymatic activity. Since NAD(P)H and INA share the nicotinic acid moiety, the inventors hypothesized that INA also binds catalase, but unlike NAD(P)H, this binding would inhibit catalase's ability to convert $H_2O_2$ to $H_2O$ and $O_2$.

The inventors found that INA inhibited catalase's enzymatic activity (FIG. 16 and Table 8). SA and INA were found to have similar dose response curves for inhibition of catalase in vivo (FIG. 16). This was determined by adding increasing concentrations of SA or INA to tobacco suspension cells (derived from cultivar Xanthi nc), as described below. The tobacco suspension cell culture was grown in the dark in MS medium at approximately 22° C. with agitation (160 rpm). Cells were maintained by diluting 10-fold every 5 days. For experimentation, 5 ml of suspension cells obtained 3 days after dilution was transferred to a 25 ml Erlenmeyer flask and agitated (100 rpm) at room temperature in the absence or presence of SA or INA which had been adjusted to pH 5.8. After 1 hr, 1 ml of the treated cell suspension was transferred to 7 ml of fresh MS medium containing SA or INA in a 10 ml beaker (density was approximately 6 mg cells per ml). Cells were maintained in suspension with a magnetic stir bar. In vivo catalase activity was determined by measuring, with an oxygen electrode, the rate of $H_2O_2$-dependent $O_2$ production immediately after addition of $H_2O_2$ to 10 mM final concentration.

To assess whether INA's inhibition of catalase was responsible for its biological activity, various biologically inactive, as well as active, analogues of INA were tested for their ability to bind SABP/catalase and inhibit its enzymatic activity (Table 8). The biological activity of the analogues, obtained from CIBA-Geigy Corporation, were determined by measuring their ability at 1 mM concentration to induce PR-1 protein synthesis in tobacco leaf disks during a 24-hour incubation and by their effectiveness in inducing resistance in cucumber to microbial pathogen infection (Smith et al. Physiol. Molec. Plant Pathol. 38: 223–235 (1991). Binding to SABP/catalase was determined by a competition assay with crude extracts prepared from tobacco leaves. Binding of INA, SA and their analogues was measured as percentage inhibition of binding of $^{14}C$-labeled SA [20 μM] in the presence of 1 mM unlabeled INA, SA or their analogues, as described by Chen and Klessig (Proc. Natl. Acad. Sci. U.S.A. 88: 8179, 1991). Inhibition of catalase activity in tobacco suspension cells was measured as described above.

TABLE 8

Inhibition by INA, SA and their analogues of catalase activity and [$^{14}C$] SA binding

| INA, SA and analogues (cpd. name or number) | Biological activity | Catalase activity | [$^{14}C$]SA binding |
|---|---|---|---|
| (INA) | + | 98 | 65 |
| (3) | + | 100 | 69 |

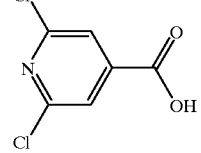

TABLE 8-continued

Inhibition by INA, SA and their analogues of catalase activity and [$^{14}$C] SA binding

| INA, SA and analogues (cpd. name or number) | Biological activity | Catalase activity | [$^{14}$C]SA binding |
|---|---|---|---|
| 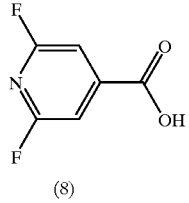 (8) | + | 48 | 63 |
| 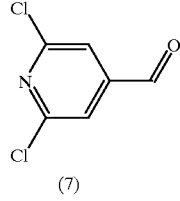 (7) | + | 79 | 25 |
| 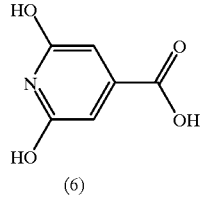 (6) | − | 25 | 19 |
| 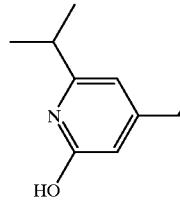 (9) | − | 15 | 11 |
| 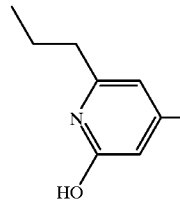 (1) | − | 4 | 7 |
| 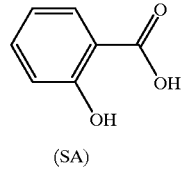 (SA) | + | 84 | 90 |
| 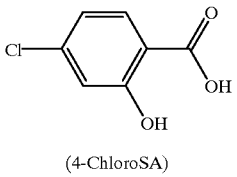 (4-ChloroSA) | + | 95 | 88 |
| 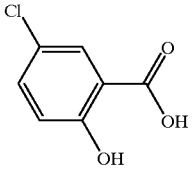 (5-ChloroSA) | + | 100 | 87 |
| 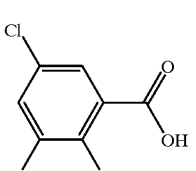 (3,5-DichloroSA) | + | 100 | 85 |
| 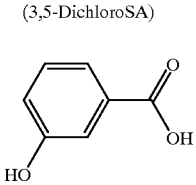 (3-HydroxyBA) | − | 0 | 1 |
| 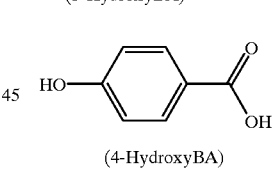 (4-HydroxyBA) | − | 0 | 0 |

As shown in Table 8, there is a close correlation between biological activity of the analogues and their ability to binding to catalase and inhibit its activity. The exception to this correlation was analogue #7 which was active in the two in vivo assays (PR-1 gene induction and inhibition of catalase) but much less active in the in vitro binding assay. A likely explanation is that the aldehyde form of INA (analogue #7) is rather inactive compared to the acidic form (INA) and in vivo the aldehyde form was converted to INA. In sum, the above dose-response analysis (FIG. 16) and pharmacological data suggest that INA and SA share the same mode of action, namely, inhibition of catalase's ability to convert $H_2O_2$ to $H_2O$ and $O_2$.

In addition, the chlorinated SA analogues 4-chlorosalicylic acid, 5-chlorosalicylic acid and 3,5-dichlorosalicylic acid were found to be potent inducers of PR-1 protein synthesis and enhanced resistance to TMV infection of N.t. cv. Xanthi nc plants as measured by reduction in lesion size compared to water-treated control plants. These SA analogues also very effectively inhibited catalase activity of tobacco suspension cells in vivo and binding of $^{14}$C-labeled SA to SABP/catalase in vitro.

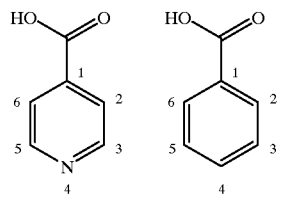

Comparison of the structure of INA and its active analogues with the structure of SA and its active analogues (Tables 6 and 8) suggests there are several common features of these compounds which allow or facilitate their binding to and inhibition of catalase activity.

Both contain a six-membered, conjugated ring and a carboxyl group. Substitution of hydrogen atoms by halide groups at the 3,4 and 5 positions of the ring (relative to the carboxyl group) do not interfere with and may enhance binding to SABP/catalase, whereas substitution of hydroxyl groups at the same positions blocks binding. Addition of a hydroxyl group at position 2 of benzoic acid (BA) appears to facilitate binding while substitution of a chloro, ethoxyl, or thiol group at this position inhibits binding (Table 2 from Chen et al., Proc. Natl. Acad. Sci. U.S.A. 90: 9533, 1993).

EXAMPLE 30

Ascorbate Peroxidase

Inhibition of peroxidase by SA and INA was determined by measuring the enzyme activities in extracts prepared from tobacco leaves in the absence or presence of 100 μM or 1000 μM SA or INA. Two grams of leaves from 6–8 week old tobacco plants (*Nicotiana tabacum* cv. Xanthi nc) grown at 22° C. in a 14 hr light cycle were homogenized under liquid nitrogen using a pestle and mortar.

To obtain ascorbate peroxidase-containing extracts, the soluble proteins were extracted by grinding the powder in 10 ml of 100 mM potassium phosphate, pH 7, containing 0.25 gM ascorbate and 1% (weight/volume) polyvinylpyrrolidone, with a small amount of quartz sand. The homogenate was centrifuged at 14,000 g for 5 min. Ammonium sulfate was added to the supernatant to 45% saturation, and the resulting suspension was stirred for an additional one hour. After centriguation at 14,000 g for 15 minutes to remove the precipitate, the ammonium sulfate concentration of the supernatant was brought to 85% saturation. The pellet resulting from centrifugation (14,000 g, 15 min.) was resuspended in extraction buffer (100 mM potassium phosphate, pH7, containing 0.25 mM ascorbate and 1% (weight/volume) polyvinylpyrrolidone) and desalted on a PD-10 column (Pharmacia) equilibrated with 50 mM potassium phosphate, pH 7, containing 100 μM ascorbate. The extract was used immediately. Ascorbate peroxidase activity was determined spectrophotometrically as described by Nakano and Asada (Plant Cell Physiol. 22: 867 (1981)) in 1 ml of a reaction mixture containing 50 mM potassium phosphate, pH 7, 0.75 μM ascorbate and 0.1 μM hydrogen peroxide. The amount of protein per assay was 30–50 μg. Oxidation of ascorbate was followed by the decrease in the absorbance at 290 nm. The reaction rates measured were linear for at least three minutes and were corrected for auto-oxidation of ascorbate in presence of $H_2O_2$.

Total guaiacol peroxidase activity was extracted with 100 mM potassium phosphate, pH 6.2, containing 1% (weight/volume) polyvinylpyrrolidone. In order to also extract the ionically bound cell wall isozymes, the extraction buffer was supplemented with 600 mM KCl. Extraction and centrifugation steps were as described for ascorbate peroxidase. After removal of cell debris and ammonium sulfate precipitation (85%), the extract was desalted against 50 mM potassium phosphate, pH 6, containing 25% glycerol. The extract could be stored at −20° C. without significant loss of peroxidase activity.

Horseradish peroxidase (1 mg; obtained from Sigma) was dissolved in 1.5 ml 200 mM potassium phosphate, pH 6.2, containing 150 mM NaCl. Following a 15 minute incubation at room temperature, the enzyme solution was centrifuged (10,000 g, 10 minutes). After buffer exchange (PD-10, equilibrated with 25 mM potassium phosphate, pH 6.2), the protein concentration was adjusted to 0.5 mg/ml.

Guaiacol peroxidase activity was determined by the method of Chance and Maehly (Methods Enzymol. 2: 764 (1955)) using guaiacol as the substrate.

The formation of tetraguaiacol was monitored at 470 nm. The reaction mixture contained 0.25% guaiacol and 100 mM hydrogen peroxide in 20 mM potassium phosphate, pH 6.2. The amount of protein per 1 ml assay was 50–80 mg. The reaction was measured for five minutes. The assay for horseradish peroxidase was identical, except that only 0.2–0.5 μg protein was used.

To determine the concentration of SA or INA required to obtain 50% inhibition of ascorbate peroxidase activity, activity was measured as described above in the presence of 750 μM ascorbate and different concentrations of SA or INA ranging from 25 μM to 500 μM. See FIG. 17. 50% inhibition was obtained at approximately 80 μM SA or 95 μM INA. The values illustrated in FIG. 17 are the mean values for three replicated assays. The specific activity at the control was 5.0 μmol min$^{-1}$mg$^{-1}$.

To assess whether SA's inhibition of catalase was responsible for its biological activity, various biologically inactive, as well as active, analogues of SA were tested for their ability to inhibit ascorbate peroxidase activity as shown in Table 10. Biological activity was based on previous studies by Conrath et al. (Proc. Natl. Acad. Sci. USA (1995) in press), White (Virology 99: 410 (1979)), van Loon (Neth. J. Plant Pathol. 89: 265 (1983)), Abad et al. (Antiviral Res. 9: 315 (1988)), and Doherty et al. (Physiol. Mol. Plant Pathol. 33: 377 (1988)). Inhibition of ascorbate peroxidase in extracts from tobacco leaves was measured as described above using 200 μM of the various analogues. The biologically active analogues were very effective inhibitors of ascorbate peroxidase activity while the biologically inactive derivatives were much poorer inhibitors.

EXAMPLE 31

Techniques for the Generation of Transgenic Plants

The following example describes and reviews techniques which are well known in the art for the expression of foreign genes in both monocotyledonous and dicotyledonous plants. These techniques are suitable for the expression of SABP/catalase in antisense (for example) in transgenic plants, and specific experimental details of such an experiment are given in Example 27.

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin (Messing & Vierra, Gene 19: 259–268 (1982); Bevan et al., Nature 304: 184–187 (1983), the bar gene which confers resistance to the herbicide phosphinothricin (White et al., Nucl Acids Res 18: 1062 (1990), Spencer et al. Theor Appl Genet 79: 625–631 (1990), the hph gene which confers resistance to the antibiotic hygromycin (Blochinger & Diggelmann, Mol Cell Biol 4: 2929–2931), and the dhfr gene, which confers resistance to methatrexate (Fling & Elwell, 1980).

Vectors suitable for Agrobacterium transformation typically carry at least one T-DNA border sequence. These include vectors such as pBIN19 (Bevan, Nucl. Acids Res. (1984) and pCIB200 (EP O 332 104).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not reply on Agrobacterium include transformation via particle bombardment, protoplast uptake (e.g. PEG and electroporation) and microinjection. The choice of vector depends largely on the preferred selection for the species being transformed. For example, pCIB3064 is a pUC-derived vector suitable for direct gene transfer technique in combination with selection by the herbicide basta (or phosphinothricin). It is described in WO 93/07278 and Koziel et al. (Biotechnology 11: 194–200 (1993)).

Requirements for Construction of Plant Expression Cassettes

Gene sequences intended for expression in transgenic plants are firstly assembled in expression cassettes behind a suitable promoter and upstream of a suitable cleavage and polyadenylation site. These expression cassettes can then be easily transferred to the plant transformation vectors described above. The manipulations of required sequences in vectors prior to their transfer to plant transformation vectors is according to techniques well known in the art.

The present invention encompasses the expression of the genes of this invention in sense or antisense orientation under the regulation of any promoter which is expressible in plants, regardless of the origin of the promoter. Furthermore, the invention encompasses the use of any plant-expressible promoter in conjunction with any further sequences required or selected for the expression of the AMS gene. Such sequences include, but are not restricted to, cleavage and polyadenylation sites, extraneous sequences to enhance expression (such as introns [e.g. Adh intron 1], vital sequences [e.g. TMV-Ω].

Promoter Selection

The selection of promoter used in expression cassettes will determine the spatial and temporal expression pattern of the construction in the transgenic plant. Selected promoters may have constitutive activity and these include the CaMV 35S promoter, the actin promoter (McElroy et al. Plant Cell 2: 163–171 (1990); McElroy et al. Mol. Gen.Genet. 231: 150–160 (1991); Chibbar et al. Plant Cell Rep 12: 506–509 (1993), and the ubiquitin promoter (Binet et al. Plant Science 79: 87–94 (1991), Christensen et al. Plant Molec. Biol. 12: 619–632 (1989); Taylor et al. Plant Cell rep. 12: 491–495 (1993)). Alternatively they may be wound-induced (Xu et al. Plant Molec. Biol 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993) and thus drive the expression of a transgene at the sites of wounding or pathogen infection. Other useful promoters are expressed in specific cell types (such as leaf epidermal cells, meosphyll cells, root cortex cells) or in specific tissues or organs (roots, leaves or flowers, for example). Patent Application WO 93/07278, for example, describes the isolation of the maize trpA gene which is preferentially expressed in pith cells. Hudspeth & Grula (Plant Molec Bio 12: 579–589 (1989) have described a promoter derived from the maize gene encoding phosphoenolpyruvate carboxylase (PEPC) with directs expression in a leaf-specific manner. Alternatively, the selected promoter may drive expression of the gene under a light-induced or other temporally-regulated promoter. A further alternative is that the selected promoter be chemically regulated. It will be appreciated that many different promoters with different expression patterns are available and well known in the art.

Transcriptional Cleavage and Polyadenylation Sites

A variety of transcriptional cleavage and polyadenylation sites are available for use in expression cassettes. These are responsible for correct processing (formation) of the 3' end of mRNAs. Appropriate transcriptional cleavage and polyadenylation sites which are known to function in plants include the CaMV 35S cleavage and polyadanylation sites, the tm1 cleavage and polyadenylation sites, the nopaline synthase cleavage and polyadenylation sites, the pea rbcS E9 cleavage and polyadenylation sites. These can be used in both monocotyledons and dicotyledons.

Seguences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop 1: 1183–1200 (1987). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990)).

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (popular)). Agrobacterium transformation typically involves the transfer of the binary vector carrying the foreign DNA of interest (e.g. pCIB200 or pCIB2001) to an appropriate Agrobacterium strain which may depend on the complement of vir genes carried by the host Agrobacterium strain either on a co-resident Ti plasmid or chromosomally (e.g. strain CIB542 for pCIB200 (Uknes et al. Plant Cell 5: 159–169 (1993)). The transfer of the recombinant binary vector to Agrobacterium is accomplished by a triparental mating procedure using E. coli carrying the recombinant binary vector, a helper E. coli strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Transformation of Monocotyledons

Transformation of most monocotyledonous species has now also become routine. Preferred techniques include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is less than 100% frequency with which separate DNA species are integrated into the genome (Schocher et al. Biotechnology 4: 1093–1096 (1986)).

Patent Applications EP 0 292 435, EP 0 392 225 and WO 93/07278 describe techniques for the preparation of callus and protoplasts of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, application WO 93/07278 and Koziel et al. (Biotechnology 11: 194–200 (1993) describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange et al., Plant Cell Rep. 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)).

Patent Application EP 0 332 581 described techniques for the generation, transformation and regeneration of Pooideae protoplasts. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993) ) using particle bombardment of immature embryos and immature embryo-derived callus.

We claim:

1. A screening method for identifying potential inducers of plant disease defense response comprising the steps of:

combining a known amount of catalse with at least one test substance which may influence catalase's enzymatic activity;

identifying a change in said catalase's enzymatic activity in the presence of said test substance; and correlating said change in said catlase's enzymatic with said test substance's potential to induce a plant disease defense response.

2. The method of claim 1 further comprising the steps of combining said test substance exhibiting a change in said catalase's enzymatic activity with a known amount of ascorbate peroxidase;

identifying a change in said ascorbate peroxidase's enzymatic activity in the presence of said test substance;

and correlating said change in said ascorbate peroxidase's enzymatic activity with said test substance's potential to induce a plant disease defense response.

3. A screening method for identifying potential inducers of plant disease defense response comprising the steps of:

combining a known amount of ascorbate peroxidase with at least one test substance which may influence ascorbate peroxidase's enzymatic activity;

identifying a change in said ascorbate peroxidase's enzymatic activity in the presence of said test substance; and correlating said change in said ascorbate peroxidase's enzymatic activity with said test substance's potential to induce a plant disease defense response.

4. The method of claim 3 further comprising the steps of combining said test substance exhibiting a change in said ascorbate peroxidase's enzymatic activity with a known amount of catalase;

identifying a change in said catalase's enzymatic activity in the presence of said test substance; and correlating said change in said catalase's activity with said test substance's potential to induce a plant disease defense response.

* * * * *

UNITED STATES PATENT AND TRADEMARK OFFICE
CERTIFICATE OF CORRECTION

PATENT NO. : 5,989,846
DATED : November 23, 1999
INVENTOR(S) : Klessig et al.

It is certified that error appears in the above-identified patent and that said Letters Patent is hereby corrected as shown below:

On the title page:

Under *Attorney, Agent, or Firm,* after "Mentlik" insert --,LLP--.
    Column 7, line 41, "thus" should read --the--.
    Column 18, line 36, "has" should read --have--.
    Column 22, line 60, "was" should read --were--.
    Column 23, line 13, "was" should read --were--.
    Column 24, line 6, after "St. Louis," insert --)--.
    Column 25, line 20, cancel "a".
    Column 29, line 52, "100 mm" should read --100 mM--.
    Column 30, line 42, after "determined" insert --by--.
    Column 35, line 14, "subject" should read --subjected--.
    Column 35, lines 25-26, "subject" should read --subjected--.
    Column 35, line 27, "contain" should read --contained--.
    Column 35, line 48, "SABPS" should read --SABPs--.
    Column 36, line 35, "BABP" should read --SABP--.
    Column 39, line 49, "PCGN" should read --pCGN--.
    Column 41, line 15, "Xanth inc" should read --Xanthi nc--.
    Column 45, line 44, "gM" should read --µm--.
    Column 50, line 31, "catlase's" should read --catalase's--.
    Column 50, line 31, after "enzymatic" insert --activity--.
    Column 50, line 61, after "catalase's" insert --enzymatic--.

Signed and Sealed this

Twenty-ninth Day of August, 2000

*Attest:*

Q. TODD DICKINSON

*Attesting Officer*      *Director of Patents and Trademarks*